US012725003B2

(12) United States Patent
Friedensohn et al.

(10) Patent No.: US 12,725,003 B2
(45) Date of Patent: Sep. 1, 2026

(54) IDENTIFICATION OF CONVERGENT ANTIBODY SPECIFICITY SEQUENCE PATTERNS

(71) Applicant: Alloy Therapeutics, Inc., Waltham, MA (US)

(72) Inventors: Simon Friedensohn, Riehen (CH); Sai Reddy, Basel (CH)

(73) Assignee: Alloy Therapeutics, Inc., Waltham, MA (US)

( * ) Notice: Subject to any disclaimer, the term of this patent is extended or adjusted under 35 U.S.C. 154(b) by 1317 days.

(21) Appl. No.: 17/442,465

(22) PCT Filed: May 2, 2020

(86) PCT No.: PCT/IB2020/054171
§ 371 (c)(1),
(2) Date: Sep. 23, 2021

(87) PCT Pub. No.: WO2020/225693
PCT Pub. Date: Nov. 12, 2020

(65) Prior Publication Data
US 2022/0164627 A1 May 26, 2022

Related U.S. Application Data

(60) Provisional application No. 62/843,010, filed on May 3, 2019.

(51) Int. Cl.
*G06N 3/02* (2006.01)
*G16B 20/20* (2019.01)
(Continued)

(52) U.S. Cl.
CPC ............... *G06N 3/02* (2013.01); *G16B 20/20* (2019.02); *G16B 20/30* (2019.02); *G16B 40/30* (2019.02)

(58) Field of Classification Search
CPC .......... G06N 3/02; G06N 3/044; G06N 3/045; G06N 3/047; G06N 3/088; G06N 7/01; G16B 20/20; G16B 20/30; G16B 40/30
See application file for complete search history.

(56) References Cited

U.S. PATENT DOCUMENTS

2019/0018019 A1 1/2019 Shan et al.
2021/0193259 A1* 6/2021 Bikard .................. G16B 20/20
(Continued)

FOREIGN PATENT DOCUMENTS

CN 108138244 6/2018
CN 108549794 9/2018
JP 2012-097107 5/2012

OTHER PUBLICATIONS

Elena Sotillo, et al.; Convergence of Acquired Mutations and Alternative Splicing of CD19 Enables Resistance to CART-19 Immunotherapy. Cancer Discov Dec. 1, 2015; 5 (12): 1282-1295. (Year: 2015).*

(Continued)

*Primary Examiner* — Olivia M. Wise
*Assistant Examiner* — Emilie A Smith
(74) *Attorney, Agent, or Firm* — Foley & Lardner LLP

(57) ABSTRACT

The present methods use a variational autoencoder (VAE) and deep generative modelling to learn meaningful representations from the immune repertoires. The system can map input sequences into a lower-dimensional latent space, which reveals a large amount of convergent sequence patterns. The system can identify patterns present in convergent clusters that are highly predictive for antigen exposure and/or antigen specificity. The system can generate, from the latent space, novel functional antibody sequence variants in-silico.

19 Claims, 23 Drawing Sheets

Specification includes a Sequence Listing.

(51) Int. Cl.
*G16B 20/30* (2019.01)
*G16B 40/30* (2019.01)

(56) References Cited

U.S. PATENT DOCUMENTS

2022/0180975 A1* 6/2022 Regev .................... G16B 40/30
2023/0019590 A1* 1/2023 Bremel .................. G16B 20/20

OTHER PUBLICATIONS

Liu, Xueliang. "Deep recurrent neural network for protein function prediction from sequence." arXiv preprint arXiv: 1701.08318 (2017). (Year: 2017).*
Communication Pursuant to Article 94(3) EPC on EP Patent Application No. 20724223.1 dated Dec. 6, 2024 (7 pages).
First Examination Report on AU Patent Application No. 2020269607 dated Nov. 28, 2024 (5 pages).
Notice of Reasons for Rejection on JP Patent Application No. 2021-561675 dated Jun. 27, 2024 (5 pages) (with English Translation).
Second Office Action on CN Patent Application No. 202080028478.9 dated Sep. 24, 2024 (22 pages) (with English translation).
Xinyuan et al., "Application of Deep Learning in Biological Mass Spectrometry and Proteomics", Progress in Biochemistry and Biophysics, 2018, pp. 1214-1223.
Davidsen, et al., "Deep generative models for T cell receptor protein sequences," eLife 8:e46935, 18 pages (2019).
Friedensohn et al., "Convergent selection in antibody repertoires is revealed by deep learning", 2020, bioRxiv, Retrieved from the Internet: https://www.biorxiv.org/content/10.110l/2020.02.25.965673vl.full.pdf, 17 pages.
International Search Report and Written Opinion for PCT/IB2020/054171 dated Aug. 3, 2020.
Jiang et al., "Variational Deep Embedding: A Generative Approach to Clustering", 2016, arxiv.org, Cornell University Library, 201 Olin Library Cornell University Ithaca, NY. 9 pages.
Poornima, "Convergent Antibody Signatures in Dengue", 2013, Cell Host & Microbe, pp. 691-700, vol. 13, No. 6.
Malley et al., "Reduction of Respiratory Syncytial Virus (RSV) in Tracheal Aspirates in Intubated Infants by Use of Humanized Monoclonal Antibody to Rsv F Protein", The Journal of Infectious Diseases, vol. 178, Issue 6, Dec. 1998, pp. 1555-1561.
Mclellan et al., "Structure of RSV Fusion Glycoprotein Trimer Bound to a Prefusion-Specific Neutralizing Antibody", Science, May 2013, vol. 340, No. 6136, pp. 1113-1117.
Notice of Reasons for Rejection on Japanese Patent Application No. 2024-155436 dated Apr. 2, 2026 (13 pages).

* cited by examiner

| Count | CDRH3 | Binding |
|---|---|---|
| 5214 | ARGYYGNSLDY | Positive |
| 687 | ARGHYGNSFDY | Positive |
| 311 | ARGKYGSSLDY | Positive |
| 207 | ARGYYVSSLDY | Positive |
| 104 | ARGGYGNSLDF | Positive |
| 64 | ARGIYGNSLDY | Positive |
| 33 | ARSGYGSSLDY | Positive |
| 26 | ARSHYGSSLDY | Positive |
| 24 | ARGGYGNSLGY | Positive |
| 20 | ARGFYGNSLAY | Positive |

b a

| Clone-ID | HC sequence | LC sequence |
|---|---|---|
| OVA1 | QVQLQQSGAELVRPGSSVKISCKASGYAFSSYWMNWVKQRPGQGLEWIGQINPGDGDTYNNGK FKGKATLTADKSSSTAYMQLNNLTSKDSAVYFCARGGYGSFAYWGQGTLVTVSA | DIVLTQSPAIMSASPGEKVTISCSASSSVSYMFWYQQKPGSSPKPWIYRTSNLASGVPARFSGSGSG TSYSLTISSMEAEDAATYYCQQYHSYPLTFGAGTKLEIK |
| OVA2 | QVQLKQSGAELVRPGASVKLSCKTSGYIFTSYWIHWVKQRSGQGLEWIARIYPGTGSSYYNEKFKG KATLTADKSSSTAYMQLSSLKSEDSAVYFCARAEYDSSYAMDFWGQGTSVTVSS | DIVLTQSPASLAVSLGQRATISCRASQSVSTSSYSFMNWYQQKPGQPPKLLIKSASNLESGVPARFS GSGSGTDFTLNIHPVEEEDTATYYCQHSWEIPLTFGAGTKLEIK |
| OVA3 | QVQLKQSGAELVRPGASVKLSCKTSGYIFTSYWIHWVKQRSGQGLEWIARIYPGTGSTYYNEKFKG KATLTADKSSSTAYMQLSSLKSEDSAVYFCARGDYGSSYFDYWGQGTTLTVSS | DIVMTQSPASLAVSLGQRATISCRASQSVSTSSYSFMHWYQQKPGQPPKLLIKSASNLESGVPARFS GSGSGTDFTLNIHPVEEEDTATYYCQHSWEIPLTFGAGTKLEIK |
| OVA4 | QVQLKQSGAELVRPGASVKLSCKTSGYIFTSYWIHWVKQRSGQGLEWIARIYPGTGSTYYNEKFKG KATLTADKSSSTAYMQLSSLKSEDSAVYFCARNGDYAMDYWGQGTSVTVSS | DIVMTQSPASLAVSLGQRATISCRASQSVSTSSYSFMHWYQQKPGQPPKLLIKYASNLESGVPARFS GSGSGTDFTLNIHPVEEEDTATYYCQHSWEIPYTFGGGTKLELK |
| OVA5 | QVQLQQPGAELVKPGASVKLSCKASGYTFTSYYMYWVKQRPGQGLEWIGEINPSNGGTNFNEKF KSKATLTVDKSSSTAYMQLSSLTSEDSAVYYCTRGGYGSFAYWGQGTLVTVSA | DILMTQSPAIMSASPGEKVTISCSASSSVSYMFWYQQKPGSSPKPWIYRTSNLASGVPARFSGSGS GTSYSLTISSMEAEDAATYYCQQYHSYPLTFGSGTKLEIK |
| OVA6 | QVQLQQSGAELVRPGASVKLSCKTSGYIFTSYWIHWVKQRSGQGLEWIARIYPGTGSTYYNEKFKG KATLTADKSSSTAYMQLSSLKSEDSAVYFCAITTVNAMDYWGQGTSVTVSS | DIQMTQSPASLAVSLGQRATISCRASQSVSTSSYSHMNWYQQKPGQPPKLLIKYASNLESGVPARF SGSGSGTDFTLNIHPVEEEDTAIYYCQHSWEMPYTFGGGTKLEIK |

FIG. 18

| | Surrogate LC sequences |
| --- | --- |
| OVA1 | DIVMTQSPAIMSASPGEKVTMTCSASSSVSYMHWYQQKSSTSPKLWIYDTSKLPSGVPGRFSGSGSGNSYSLTISSMEAEDVATYYCFQGSGYPLTFGAGTKLEIK |
| OVA5 | DIVMTQSPSSMYASLGERVTITCKASQDIKSYLSWFQQKPGKSPKTLIYRANRLVDGVPSRFSGSGSGQDYSLTISSLEYEDMGIYYCLQYDEFPYTFGGGTKLEIK |
| | DIQMTQSPSSMYASLGERVTITCKASQDINSYLSWFQQKPGKSPKTLIYRANRLVDGVPSRFSGSGSGQDYSLTISSLEYEDMGIYYCLQYDEFPYTFGGGTKLEIK |
| | DIVLTQSHKFMSTSVGDRVSITCKASQDVGSAVAWYQQKPGQSPKLLIYWASTRRTGVPDRFTGSGSGTDFTLTINNVQSEDLADYFCHQYNTYSLTFGAGTKLEIK |
| | DIVMTQSPAIMSASPGEKVTMTCSASSSVSYMYWYQQKPGSSPRLLIYDTSNLASGVPVRFSGSGSGTSYSLTISRMEAEDAATYYCQQWSSYPPTFGSGTKLEIK |
| | DIVITQSPAIMSASPGEKVTMTCSASSSVSYMHWYQQKSSTSPKLWIYDTSKLVSGVPGRFSGSGSGNSYSLTISSMEAEDVATYYCFQGSGYPLTFGAGTKLEIK |
| | DIVLTQSPAIMSASPGEKVTMTCSASSSVRYMCWYQQKSSTSPKLWIYDTSKLASGVPGRFSGSGSGNSYSLTIGSMEAEDVATYYCFQGSGYPLTFGAGTKLELK |

FIG. 19

| | HC sequence | LC sequence |
|---|---|---|
| RSV1 | EVQLQQSGAELVRSGASVKLSCTASGFNIKDYYIHWVKQRPEQGLEWIGWIDPENGDTEYAPKFQDKATMTADTSSNTAYLQLSSLTSGDTAVYYCNAWDGNLDYWGQGTSVTVSS | DIQMTQTPLSLPVSLGNQASISCRSSQSIVHSDGNTYLEWYLQKPGQSPKLLIYKVSNRFSGVPDRFSGSGSGTDFTLKISRVEAEDLGVYYCFQGSHVPRTFGGGTKLEIK |
| RSV2 | QVTLKESGPGILQPSQTLSLTCSFSGFSLSTSGMGVSWIRQPSGKGLEWLAHIYWDDDKRYNPSLKSRLTISKDTSRNQVFLKITSVDTADTATYYCARRSYGSSLDYWGQGTTLTVSS | DIVMTQTTSSLSASLGDRVTISCRSSQDISNYLNWYQQKPDGTVKLLIYYTSRLHSGVPSRFSGSGSGSDYSLTITNLEQEDIATYFCQQGDTLPYTFGGGTKLEIK |
| RSV3 | QVQLKESGPGLVAPSQSLSITCTVSGFSLTDYGVNWVRQPPGKGLEWLGMIWGDGSTDYNSALKSRLSISKDISKSQVFLKMNSLQTDDTAKYYCARGNYGNSLDYWGQGTTLTVSS | DIVMTQSPASQSASLGESVTITCLASQTIGKWLAWYQQKPGKSPQLLIYAATILADGVPSRFSGSGSGTKFSFKISSLQAEDFVSYYCQQLYSTPLTFGGGTKLEIK |

FIG. 20

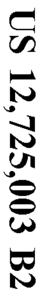

| Surrogate LC sequences | |
| --- | --- |
| RSV1 | DILMTQSPLSLPVSLGDQVSISCRSSQSIVHSNGNTYLEWYLQKPGQSPKLLIYKVSNRFSGVPDRFSGSGSGTDFTLKISRVEAEDLGVYYCFQGSHVPRTFGGGTKLEIK |
| RSV2 | DIVMTQTTSSLSASLGDRVTISCRASQDISNYLNWYQQKPDGTVKLLIYYTSRLHSGVPSRFSGSGSGTDYSLTISNLEQEDIATYFCQQGNTLPWTFGGGTKLELK |
| RSV3 | DIQINQSPASQSASLGESVTITCLASQTIGKWLAWYQQKPGKSPQLLIYAATSLADGVPSRFSGSGSGTKFSFKISSLQAEDFVSYYCQQLYSTPLTFGGGTKLEIK |

FIG. 21

| Antigen | V-Gene | J-Gene | CDR1 | CDR2 | CDR3 | Public Clone | Convergent GMM-VAE | Binder |
|---|---|---|---|---|---|---|---|---|
| OVA1 | IGHV1-80 | IGHJ3 | GYAFSSYW | INPGDGDT | ARGGYGSFAY | No | Yes(146) | Yes |
| OVA2 | IGHV1-76 | IGHJ4 | GYIFTSYW | IYPGTGSS | ARAEYDSSYAMDF | No | Yes(98) | Yes |
| OVA3 | IGHV1-76 | IGHJ2 | GYIFTSYW | IYPGTGST | ARGDYGSSYFDY | Yes | Yes(142) | Yes |
| OVA4 | IGHV1-76 | IGHJ4 | GYIFTSYW | IYPGTGST | ARNGDYAMDY | No | Yes(150) | Yes |
| OVA5 | IGHV1-53 | IGHJ3 | GYTFTSYY | INPSNGGT | TRGGYGSFAY | No | Yes(119) | Yes |
| OVA6 | IGHV1-76 | IGHJ4 | GYIFTSYW | IYPGTGST | AITTVNAMDY | No | Yes(150) | Yes |
| RSV-F1 | IGHV14-4 | IGHJ4 | GFNIKDYY | IDPENGDT | NAWDGNLDY | No | Yes(136) | Yes |
| RSV-F2 | IGHV8-12 | IGHJ2 | GFSLSTSGMG | IYWDDDK | ARRSYGSSLDY | Yes | Yes(60) | Yes |
| RSV-F3 | IGHV2-6-7 | IGHJ2 | GFSLTDYG | IWGDGST | ARGNYGNSLDY | No | Yes(199) | Yes |
| RSV-F4 | IGHV9-2-1 | IGHJ3 | GYTFTDYS | INTETGEP | ARGGNPAWFAY | No | Yes(98) | NA |

FIG. 22

IDENTIFICATION OF CONVERGENT ANTIBODY SPECIFICITY SEQUENCE PATTERNS

CROSS-REFERENCE TO RELATED APPLICATIONS

This application is a U.S. National Stage under 35 U.S.C. § 371 of International Patent Application No. PCT/IB2020/054171, filed May 2, 2020 and designating the United States, which claims priority under 35 U.S.C. § 119 to U.S. Provisional Patent Application No. 62/843,010, filed May 3, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Jul. 15, 2020, is named 122043-0105_SL.txt and is 72,119 bytes in size.

BACKGROUND OF THE DISCLOSURE

Deep sequencing of antibody repertoires can be used in immunology, immunodiagnostics, and the drug discovery process. However, identification of relevant information in these large datasets remains challenging. One central and elusive question is the extent to which antigen exposure results in convergent selection of antibody sequences in different individuals.

SUMMARY OF THE DISCLOSURE

The present solution can use variational autoencoders (VAEs), a deep generative modelling approach, to provide meaningful representations from immune repertoires of mammalian subjects, including a subject exposed to antigen. Exemplary data is provided herein demonstrating application of this approach to antibody repertoires of immunized mice. The system can map antibody repertoires into a lower-dimensional latent space, which reveals a large amount of convergent sequence patterns. The system can use a linear classifier and a combination of a variational autoencoder (VAE) with a mixture model to identify patterns present in convergent clusters that are predictive for antigen exposure. In some embodiments, the system further comprises use of variational deep embedding (VaDE). In some embodiments, the mixture model is a Gaussian mixture model. The system can also use a linear classifier and a VAE, followed by separate clustering step in latent space, to identify patterns present in convergent clusters that are predictive for antigen exposure. Convergent antibody sequences can then be expressed in a recombinant antibody expression system (e.g., as full-length IgG in a mammalian display system) and demonstrated to be antigen-specific using techniques, such as flow cytometry and enzyme-linked immunosorbent assays (ELISAs). The system can also elucidate the convergent sequence space by generating thousands of novel and functional variants in-silico.

According to at least one aspect of the disclosure, a method can include providing, to a candidate identification system, a plurality of input amino acid sequences that represent antigen binding portions of an antibody. The method can include transforming, by an encoder executed by the candidate identification system, the plurality of input amino acid sequences into a latent space. The method can include determining, by a clustering engine executed by the candidate identification system, a plurality of sequence clusters within the latent space. The method can include identifying, by the clustering engine, a convergent cluster. The method can include selecting, by a candidate generation engine executed by the candidate identification system, a sample within the latent space defined by the convergent cluster. The method can include generating, by the candidate generation engine using a decoder, a candidate sequence based on the sample within the latent space.

In some implementations, the decoder can include a plurality of long short-term recurrent neural networks and generating the candidate sequence can include providing the sample to each of the plurality of long short-term recurrent neural networks. In some implementations, transforming the plurality of input amino acid sequences into the latent space can include transforming the plurality of input amino acid sequences into the latent space with a linear classifier and a combination of a variational autoencoder with a mixture model. In some implementations, the system can use variational deep embedding (VaDE). In some implementations, the system can use one or more dense layers or long short-term memory layers. Determining the plurality of sequence clusters further comprises determining the plurality of sequence clusters with a mixture model such as Gaussian Mixture Modeling (GMM).

In some implementations, a system can include a memory storing processor executable instructions and one or more processors. The system can receive, by an encoder executed by the one or more processors, a plurality of input amino acid sequences that represent antigen binding portions of an antibody. The system can transform, by the encoder, the plurality of input amino acid sequences into a latent space. The system can determine, by a clustering engine executed by the one or more processors, a plurality of sequence clusters within the latent space. The system can identify, by the clustering engine, a convergent cluster. The system can select, by a candidate generation engine executed by the one or more processors, a sample within the latent space defined by the convergent cluster. The system can generate, by the candidate generation engine, a candidate sequence based on the sample within the latent space.

In some implementations, candidate generation engine can include a decoder having a plurality of long short-term recurrent neural networks. The encoder can transform the plurality of input amino acid sequences into the latent space with a linear classifier and a combination of a variational autoencoder with a mixture model. In some implementations, the system can use variational deep embedding (VaDE). The clustering engine can determine the plurality of sequence clusters with a mixture model such as GMM.

The input amino acid sequences can be from any mammalian subject, including human and non-human animals. The input amino acid sequences can be from healthy subjects or subjects having a disease or condition (e.g. pathogenic infection, cancer, autoimmune disorder, allergic reaction, or inflammation). The input amino acid sequences can be from subjects previously exposed to an antigen. The input amino acid sequences can be from healthy subjects previously having a disease or condition (e.g. pathogenic infection, cancer, autoimmune disorder, allergic reaction, inflammation, or inflammatory disease). The input amino acid sequences can be from immunized subjects, e.g. subjects that have received a vaccine.

The input amino acid sequences can include any antigen binding portion of an antibody. In some embodiments, the input amino acid sequences include one or more complementarity determining regions (CDRs). In some embodiments, the input amino acid sequences include one or more heavy chain CDRs, e.g. CDRH1, CDRH2, CDRH3, or any combination thereof. In some embodiments, the input amino acid sequences include one or more light chain CDRs, e.g. CDRH1, CDRH2, CDRH3, or any combination thereof. In some embodiments, the input amino acid sequences include one or more heavy chain CDRs and one or more heavy chain CDRs. In some embodiments, the input amino acid sequences include one or more framework regions of the heavy and/or light chain variable regions. In some embodiments, the input amino acid sequences include a full-length heavy chain variable region. In some embodiments, the input amino acid sequences include a full-length light chain variable region. In some embodiments, the input amino acid sequences include one or more constant regions of the heavy and/or light chain. In some embodiments, the input amino acid sequences include a full-length heavy chain or an antigen binding portion thereof. In some embodiments, the input amino acid sequences include a full-length light chain or an antigen binding portion thereof.

Also provided herein are proteins or peptides comprising an amino acid sequence generated by the methods provided herein. In some embodiments, the generated amino acid sequence is a heavy chain or a light chain of an antibody, or any portion thereof. In some embodiments, the generated amino acid sequence comprises one or more complementarity determining regions (CDRs). In some embodiments, the generated amino acid sequence comprises a CDRH1, CDRH2, CDRH3 or any combination thereof. In some embodiments, the generated amino acid sequence comprises a CDRL1, CDRL2, CDRL3 or any combination thereof. In some embodiments, the protein or peptide comprising an amino acid sequence generated herein is an antibody or fragment thereof. In some embodiments, the protein or peptide comprising an amino acid sequence generated herein is a full length antibody. In some embodiments, the protein or peptide comprising an amino acid sequence generated herein is a fusion protein comprising one or more portions of an antibody. In some embodiments, the protein or peptide comprising an amino acid sequence generated herein is an scFv or an Fc fusion protein. In some embodiments, the protein or peptide comprising an amino acid sequence generated herein is a chimeric antigen receptor. In some embodiments, the protein or peptide comprising an amino acid sequence generated herein is a recombinant protein. In some embodiments, the protein or peptide comprising an amino acid sequence generated herein binds to an antigen. In some embodiments, the antigen is associated with a disease or condition. In some embodiments, the antigen is a tumor antigen, an inflammatory antigen, pathogenic antigen (e.g., viral, bacterial, yeast, parasitic). In some embodiments, the protein or peptide comprising an amino acid sequence generated herein has one or more improved properties compared to a protein or peptide comprising the input amino acid sequence. In some embodiments, the protein or peptide comprising an amino acid sequence generated herein has improved affinity for an antigen compared to a protein or peptide comprising the input amino acid sequence. In some embodiments, the protein or peptide comprising an amino acid sequence generated herein can be administered to treat an inflammatory disease, infectious disease, cancer, genetic disorder, organ transplant rejection, autoimmune disease or an immunological disorder. In some embodiments, the protein or peptide comprising an amino acid sequence generated herein can be used for the manufacture of a medicament to treat an inflammatory disease, infectious disease, cancer, genetic disorder, organ transplant rejection, autoimmune disease and immunological disorder. Also provided herein are cells comprising one more proteins or peptides comprising an amino acid sequence generated herein. The cell can be a mammalian cell, a bacterial cell, a yeast cell or any cell that can express a protein or peptide comprising an amino acid sequence generated herein. The cell can be an immune cell, such as a T cell (e.g., a CAR-T cell). In some embodiments, the protein or peptide comprising an amino acid sequence generated herein can be used to detect an antigen in a biological sample.

Also provided herein are proteins or peptides comprising an amino acid sequence shown any of FIGS. 10, 12-13 or FIGS. 18-22 or one or more CDR sequences of an amino acid sequence shown any of FIGS. 10, 12-13 or FIGS. 18-22. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is an antibody or fragment thereof. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is a full length antibody. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is a fusion protein comprising one or more portions of an antibody. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is an scFv or an Fe fusion protein. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is a chimeric antigen receptor. In some embodiments, the protein or peptide comprising an amino acid sequence shown any of FIGS. 10, 12-13 or FIGS. 18-22 or one or more CDR sequences of an amino acid sequence shown any of FIGS. 10, 12-13 or FIGS. 18-22 is a recombinant protein.

In some embodiments, the protein or peptide comprising an amino acid sequence shown any of FIGS. 10, 12 or FIGS. 18-19 or one or more CDR sequences of an amino acid sequence shown any of FIGS. 10, 12 or Tables 2-3 binds to an ovalbumin antigen. In some embodiments, the protein or peptide comprising an amino acid sequence shown any of FIGS. 10, 12 or FIGS. 18-19 or one or more CDR sequences of an amino acid sequence shown any of FIGS. 10, 12 or FIGS. 18-19 can be used to detect an ovalbumin antigen (e.g., in a biological sample).

In some embodiments, the protein or peptide comprising an amino acid sequence shown any of FIG. 10, 13, 20 or 21 or one or more CDR sequences of an amino acid sequence shown any of FIG. 10, 13, 20 or 21 binds to an RSV-F antigen. In some embodiments, the protein or peptide comprising an amino acid sequence shown any of FIG. 10, 13, 20 or 21 or one or more CDR sequences of an amino acid sequence shown any of FIG. 10, 13, 20 or 21 can be administered to treat a respiratory syncytial virus infection. In some embodiments, the protein or peptide comprising an amino acid sequence shown any of FIG. 10, 13, 20 or 21 or one or more CDR sequences of an amino acid sequence shown any of FIG. 10, 13, 20 or 21 can be used for the manufacture of a medicament to treat a respiratory syncytial virus infection. In some embodiments, the protein or peptide comprising an amino acid sequence shown any of FIG. 10, 13, 20 or 21 or one or more CDR sequences of an amino acid sequence shown any of FIG. 10, 13, 20 or 21 can be used to detect an RSV-F antigen (e.g., in a biological sample).

Also provided herein are cells comprising one more proteins or peptides comprising an amino acid sequence shown any of FIGS. 10, 12, 13 or FIGS. 18-22 or one or more CDR sequences of an amino acid sequence shown any of FIGS. 10, 12, 13 or FIGS. 18-22. The cell can be a mammalian cell, a bacterial cell, a yeast cell or any cell that can express a protein or peptide comprising an amino acid sequence shown any of FIGS. 10, 12, 13 or FIGS. 18-22 or one or more CDR sequences of an amino acid sequence shown any of FIGS. 10, 12, 13 or FIGS. 18-22. The cell can be an immune cell, such as a T cell (e.g., a CAR-T cell).

The foregoing general description and following description of the drawings and detailed description are exemplary and explanatory and are intended to provide further explanation of the invention as claimed. Other objects, advantages, and novel features will be readily apparent to those skilled in the art from the following brief description of the drawings and detailed description.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings:

As illustrated in FIG. 2, the VAE includes both dense layers (e.g., non-linear activation function) as well as linear layers. The Dense layer can include, for example, filters or units ranging in quantity from 256 to 512 or some other amount. The linear layers can include 10 units, or some other number of units.

FIG. 10B discloses SEQ ID NOS 76-81, 79, 82-83, 79, 82, 84, 47-48, 85, 79, 82, and 86, and FIG. 10D discloses SEQ ID NOS 87-95, all respectively, in order of appearance.

FIG. 18 illustrates sequences confirmed to bind OVA. Figure discloses the "HC" sequences as SEQ ID NOS 96-101 and the "LC" sequences as SEQ ID NOS 117-122, all respectively, in order of appearance.

FIG. 19 illustrates surrogate $V_L$ chain sequences for OVA1 and OVA5. Figure discloses SEQ ID NOS 123-129, respectively, in order of appearance.

FIG. 20 illustrates sequences confirmed to bind RSV. Figure discloses the "HC" sequences as SEQ ID NOS 102-104 and the "LC" sequences as SEQ ID NOS 130-132, all respectively, in order of appearance.

FIG. 21 illustrates surrogate $V_L$ chain sequences for RSV1, 2 and 3(SEQ ID NOS 133-135, respectively, in order of appearance.

FIG. 22 illustrates convergent antibody sequences screened for antigen-binding. The table shows convergent sequences experimentally screened for antigen-binding. The three rightmost columns indicate whether a sequence could have been identified by the respective method. A sequence would have been discovered as public clone if it is shared with at least one other mouse in its cohort, but was not observed in any other antigen cohort. Number in parentheses indicates the number of sequences found in the convergent cluster. Figure discloses the "CDR1" sequences as SEQ ID NOS 76, 79, 79, 79, 47, 79, 87, 90, 93, and 136, the "CDR2" sequences as SEQ ID NOS 77, 80, 82, 82, 48, 82, 88, 91, 94, and 137, and the "CDR3" sequences as SEQ ID NOS 138-143, 38-39, 53, and 40, all respectively, in order of appearance.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

The methods described herein use variational autoencoders (VAEs), a deep generative modelling approach to provide meaningful representations from immune repertoires of mammalian subjects, including subjects exposed to an antigen. The system can map antibody repertoires into a lower-dimensional latent space, which reveals a large amount of convergent sequence patterns. In some embodiments, the system can use a linear classifier and variational deep embedding (VaDE) to identify patterns present in convergent clusters that are predictive for antigen exposure. In some embodiments, a statistical test such as a t-test, Fisher's exact test or a permutation-based test is used to test for statistical significance are used in place of the linear classifier. Convergent antibody sequences can then be expressed in a recombinant expression system (e.g., as full-length IgG in a mammalian display system) and demonstrated to be antigen-specific using techniques, such as flow cytometry and enzyme-linked immunosorbent assays (ELISAs). The system can also elucidate the convergent sequence space by generating thousands of novel and functional variants in-silico. The methods can be applied to the development of therapeutic and diagnostic (target identifying) antibody agents with improved properties.

Figure 1:
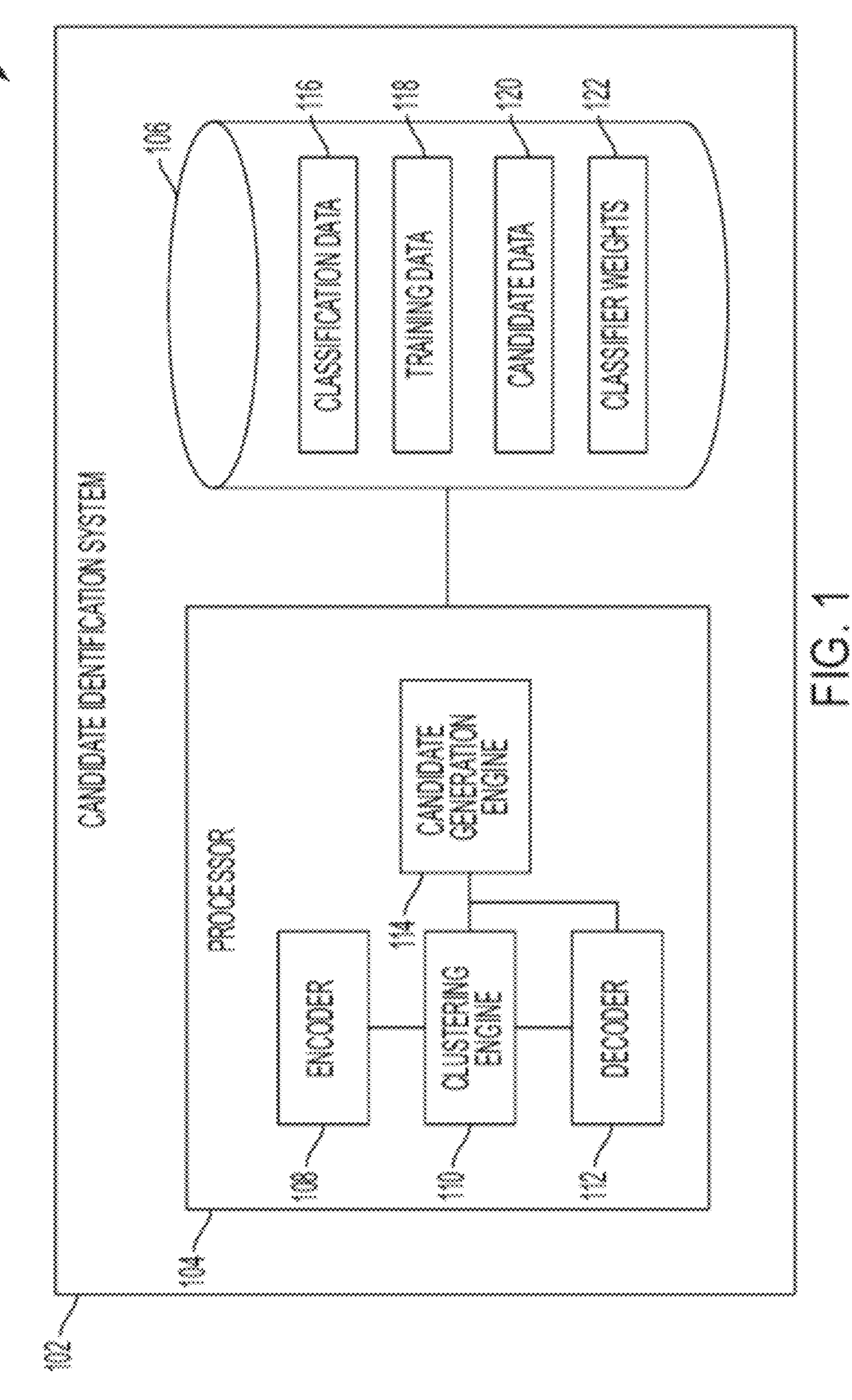
FIG. 1 illustrates a block diagram of an example candidate identification system.

FIG. 1 illustrates a block diagram of an example system 100 to generate in silico sequences, which can be referred to as candidate sequences. The candidate identification system 102 can include one or more processors 104 and one or more memories 106. The processors 104 can execute processor-executable instructions to perform the functions described herein. The processor 104 can execute an encoder 108, a clustering engine 110, a decoder 112, and a candidate selection engine 114. The memory 106 can store processor-executable instructions, generate data, and collected data. The memory 106 can store one or more classifier weights 122. The memory 106 can also store classification data 116, training data 118, and candidate data 120.

The system 100 can include one or more candidate identification systems 102. The candidate identification system 102 can include at least one logic device, such as the processors 104. The candidate identification system 102 can include at least one memory element 106, which can store data and processor-executable instructions. The candidate identification system 102 can include a plurality of computing resources or servers located in at least one data center. The candidate identification system 102 can include multiple, logically-grouped servers and facilitate distributed computing techniques. The logical group of servers may be referred to as a data center, server farm, or a machine farm. The servers can also be geographically dispersed. The candidate identification system 102 can be any computing device. For example, the candidate identification system 102 can be or can include one or more laptops, desktops, tablets, smartphones, portable computers, or any combination thereof.

The candidate identification system 102 can include one or more processors 104. The processor 104 can provide information processing capabilities to the candidate identification system 102. The processor 104 can include one or more of digital processors, analog processors, digital circuits to process information, an analog circuit designed to process information, a state machine, and/or other mechanisms for electronically processing information. Each processor 104 can include a plurality of processing units or processing cores. The processor 104 can be electrically coupled with the memory 106 and can execute the encoder 108, clustering engine 110, decoder 112, and candidate generation engine 114.

The processor 104 can include one or more microprocessors, application-specific integrated circuits (ASIC), field-programmable gate arrays (FPGA), or combinations thereof. The processor 104 can be an analog processor and can include one or more resistive networks. The resistive network can include a plurality of inputs and a plurality of outputs. Each of the plurality of inputs and each of the plurality of outputs can be coupled with nanowires. The nanowires of the inputs can be coupled with the nanowires of the outputs via memory elements. The memory elements can include ReRAM, memristors, or PCM. The processor 104, as an analog processor, can use analog signals to perform matrix-vector multiplication.

The candidate identification system 102 can include one or more encoders 108. The encoder 108 can be an application, applet, script, service, daemon, routine, or other executable logic to encode an input sequence to a latent space. The encoder 108 can include a neural network auto-encoder. The encoder 108 is described further in relation to FIG. 3, among others. As an overview, the encoder 108 can receive unlabeled input sequences map (or encode) the input sequences to a lower dimension space. The encoder 108 can encode the input sequences to a lower dimension space using, for example, a variational autoencoder (VAE). In some embodiments, the encoder uses variational deep embedding (VaDE). The encoder 108 can map the input sequences to a, for example, five dimension space. In some embodiments, the encoder can jointly optimize a deep generative model together with a mixture model, such as a Gaussian mixture model (GMM)-based clustering of the latent space.

The candidate identification system 102 can include one or more clustering engines 110. The clustering engine 110 can be an application, applet, script, service, daemon, routine, or other executable logic to determine clusters within the latent space. The clustering engine 110 can use K-means clustering to identify the clusters generated by the encoder 108 from the input sequences in the latent space. The clustering engine 110 can use Gaussian Mixture Modeling (GMM) to identify the clusters in the latent space.

The candidate identification system 102 can include one or more decoders 112. The decoder 112 can be an application, applet, script, service, daemon, routine, or other executable logic to decode or otherwise create an output sequence from an input in the latent space. The decoder 112 is further described in relation to FIG. 4, among others. The decoder 112 can receive a sample from the latent space and reconstruct a sequence (e.g., CDR1, CDR2, or CDR3). For example, the decoder 112 can convert a latent space sample into a one-hot encoded matrix that represents the sequence of CDR1, CDR2, or CDR3. In some implementations, the decoder 112 can include a plurality of different neural networks. For example, the decoder 112 can include a different neural network for each of the sequences generated from a latent space sample. The decoder 112 can include a different neural network to generate each of the CDR1, CDR2, and CDR3 sequences. The neural networks of the decoder 112 can be long short-term recurrent neural networks.

The candidate identification system 102 can include a candidate generation engine 114. From the clusters identified by the clustering engine 110, and using the decoder 112, the candidate generation engine 114 can generate in silico output sequences. For example, the candidate generation engine 114 can select a sample from the latent space. The candidate generation engine 114 can select the sample from within a defined cluster within the latent space. The candidate generation engine 114 can provide the sample to the decoder 112 to generate an output, in silico sequence, which the candidate generation engine 114 can store into the memories as candidate data 120.

The candidate identification system 102 can include one or more memories 106. The memory 106 can be or can include a memory element. The memory 106 can store machine instructions that, when executed by the processor 104 can cause the processor 104 to perform one or more of the operations described herein. The memory 106 can include but is not limited to, electronic, optical, magnetic, or any other storage devices capable of providing the processor 104 with instructions. The memory 106 can include a floppy disk, CD-ROM, DVD, magnetic disk, memory chip, ROM, RAM, EEPROM, EPROM, flash memory, optical media, or any other suitable memory from which the processor 104 can read instructions. The instructions can include code from any suitable computer programming language such as, but not limited to, C, C++, C #, Java, JavaScript, Perl, HTML, XML, Python, and Visual Basic.

The candidate identification system 102 can store classifier weights 122 in the memory 106. The classifier weights 122 can be a data structure that includes the weights and biases that define the neural networks of the encoder 108 and the decoder 112. Once trained, the classification engine 108 can store the classifier weights 122 to the memory 106 for later retrieval and use generating in silico sequences, for example.

During a training phase, the encoder 108 and decoder 112 can process training data 118 to generate the weights and biases for one or more of the machine learning models within the encoder 108 and decoder 112. Once trained, the encoder 108 and decoder 112 can store the weights and biases as the classifier weights 122 in the memory 106. The generation of the training data and training of the encoder 108 and decoder 112 is described further in relation to the memory 106, training data 118, and examples, below. Once the encoder 108 and the decoder 112 are trained, the weights and biases can be saved to the memory 106 as classifier weights 122. The models (e.g., the convolution neural network, dense layers and the LSTM neural network) of the classification engine 108 are described further in relation to FIGS. 2 and 3, among others.

Figure 2:
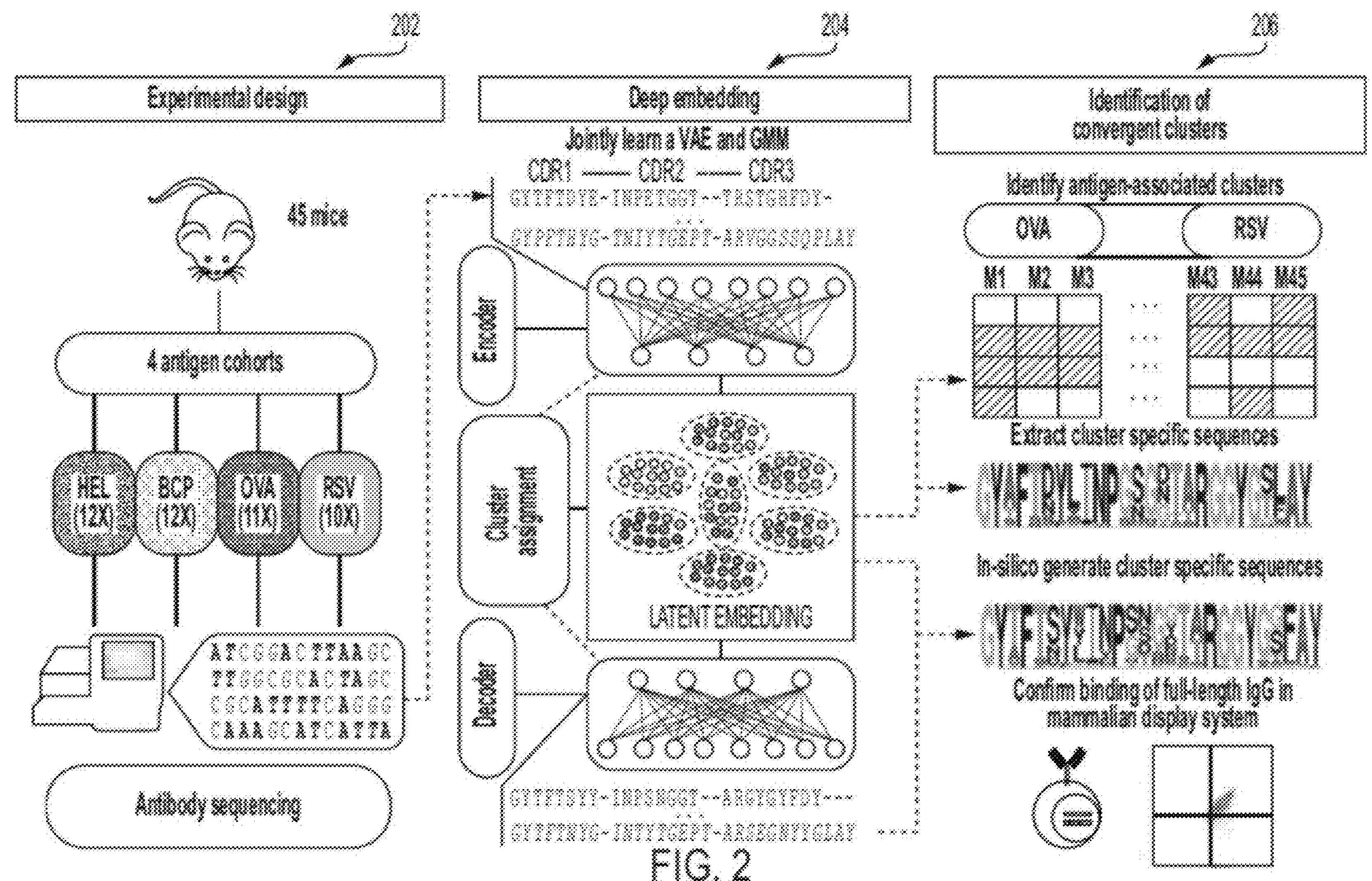
FIG. 2 illustrates flow diagram for generating in silico sequences. Antibody repertoires from the bone marrow of 45 BALB/c mice immunized with various antigens are sequenced. Antibody sequences are then used to train a deep generative model which is able to both generate novel sequences and assign input sequences to distinct clusters based on their latent embedding. Cluster assignments are used to identify sequences that are heavily enriched in a specific repertoire or antigen cohort. Natural and in silico generated sequences from antigen-associated clusters are expressed as full-length IgG and verified as binding antibodies. Figure discloses SEQ ID NOs 41-46, 37 and 47-52, respectively, in order of appearance.

FIG. 2 illustrates a flow diagram 200 for generating in silico sequences using the system illustrated in FIG. 1, for example. The flow diagram 200 includes three phases. During a first phase 202, training or testing data is generated. During a second phase 204, deep embedding can be performed to train the encoder 108. During a third phase 206, the candidate generation engine 114 can identify antigen associated clusters and then generate in silico sequences. For example, and as described further in relation to the examples section, antibody repertoires from the bone marrow of 45 BALB/c mice immunized with various antigens can be sequenced to generate training data 118. The candidate identification system 102 can use the training data 118 to train the encoder 108 and decoder 112 during the second phase 204. The trained encoder 108 can assign an input sequence to a distinct cluster based on the sequence's latent embedding. During the third phase 306, the candidate generation engine 114 can identify clusters that are enriched in a specific repertoire or antigen cohort. The candidate generation engine 114 can generate in silico sequences from antigen-associated clusters.

Figure 3:
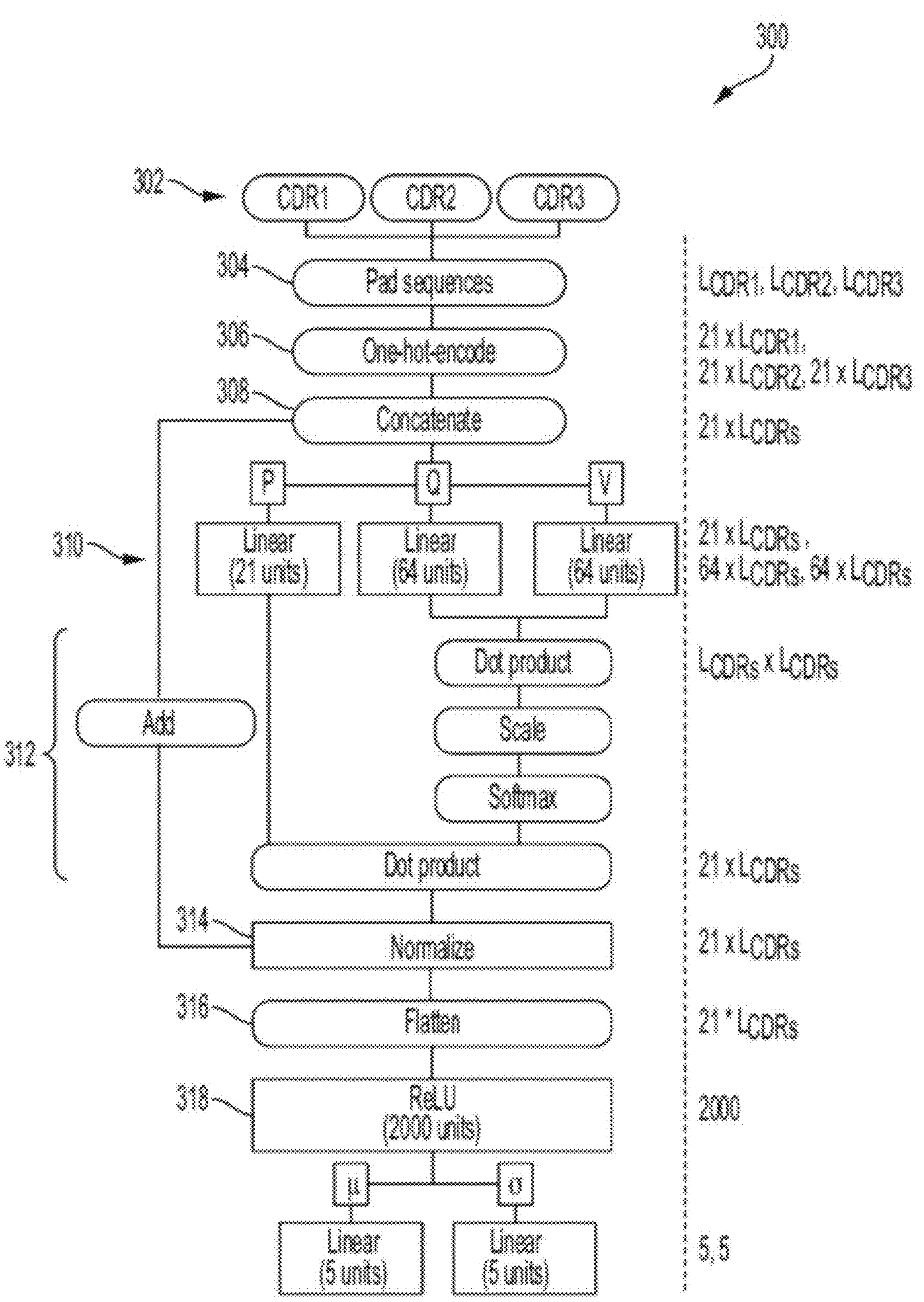
FIG. 3 illustrates an example encoder architecture that can be used in the system illustrated in FIG. 1.

FIG. 3 illustrates an example architecture 300 for the encoder 108. The encoder 108 can receive an input 302 at a first layer of the architecture 300. While FIG. 3 illustrates the input a sequence that includes the sequence for CDR1, CDR2, and CDR3, the input sequence could be any other sequence. The architecture 300 can include a padding layer 304. The padding layer 304 can zero-pad, dash-pad, or otherwise pad the input sequence such that all input sequences have the same length. For example, different variations of CDR1, CDR2, or CDR3 may have different sequence lengths. The padding layer 304 can add zeros, dashes, or other values to the end of variants that have a length shorter than the longest variant for each of the respective CDR1, CDR2, and CDR3 sequences. The each sequence exiting the padding layer 204 can have a predetermined length (or size). The architecture 300 can include a one-hot encoding layer 306 that convert the padded input sequence (output from the padding layer 304) into a one-hot encoded matrix. The one-hot encoding layer 306 can generate a one-hot encoded matrix that includes, for example, a row for each position of the padded input sequence. Each column of the one-hot encoded matrix can correspond to a different possible amino acid that can fill each respective value of the padded input sequence. In this example, as there are twenty amino acids and another column for the padded value (e.g., 0) added to the sequence, the one-hot encoded matrix includes twenty-one columns. Each row of the one-hot encoded matrix includes a 1 in the column corresponding to the amino acid present in the respective value of the padded input sequence. In some implementations, the one-hot encoding layer 306 can be an encoding layer that can use encodings different than one-hot encodings, such as BLOSUM26 or Blomap.

The architecture 300 can include a concatenation layer 308 that concatenate the one-hot encode matrix of CDR1, CDR2, and CDR3 (in this example) into a single, one-hot encoded matrix.

The architecture 300 can include a plurality of interconnected layers 310, which can be trainable layers. Each of the layers 310 can include one or more neurons. As illustrated in FIG. 3, a portion of the layers 310 can include 21 neurons and a portion of the layers 310 can include 64 units. The architecture 300 can include a plurality of operational layers 312, which can combine or otherwise perform mathematical operations on the outputs from the layers 310. The architecture 300 can include a trainable normalization layer 314. The architecture 300 can include a layer 316 that flattens the output of the normalization layer 314 to generate an output vector, which can be fully interconnected with a layer 318 including a plurality of rectified linear units (ReLUs).

Figure 4:
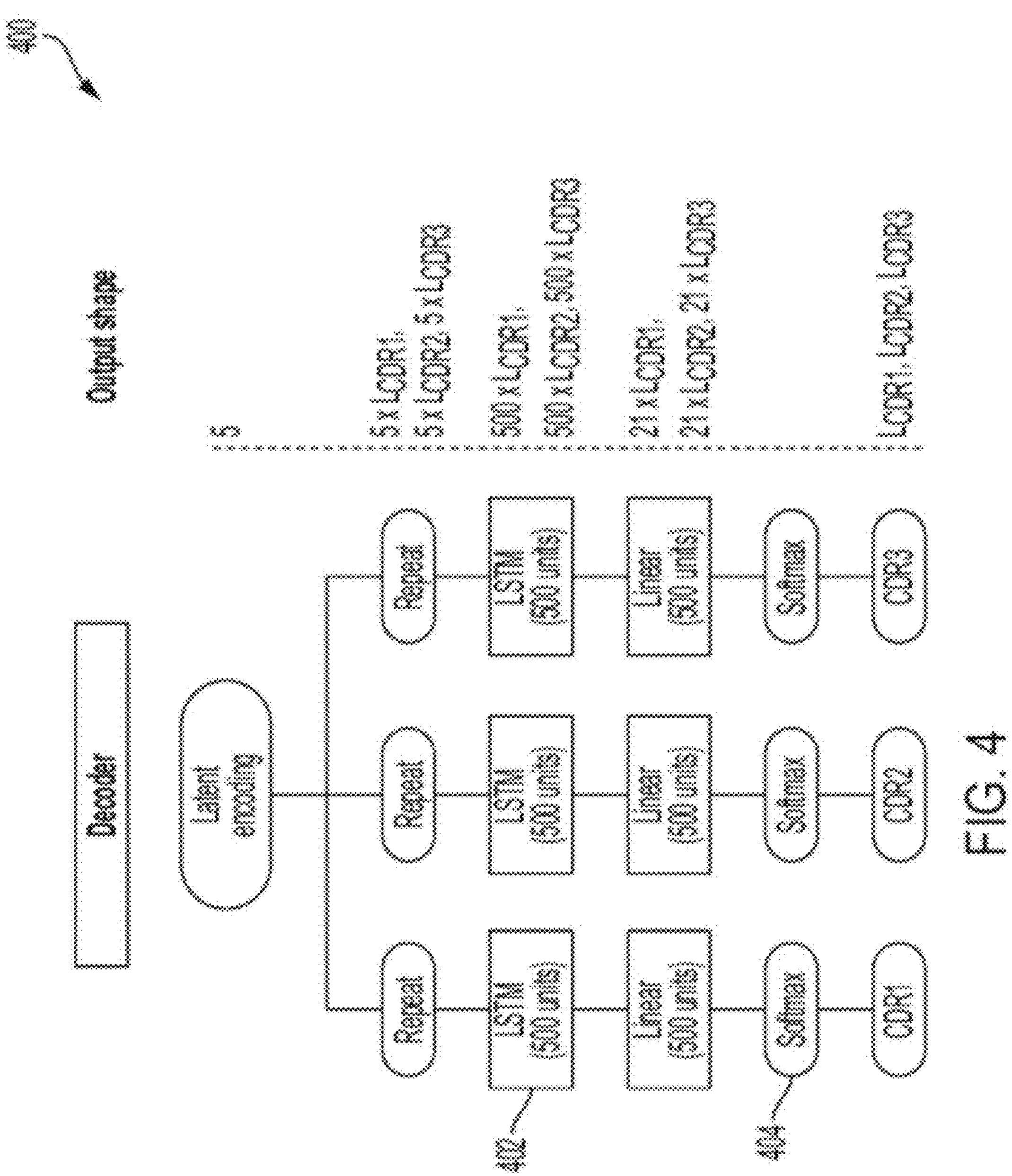
FIG. 4 illustrates an example decoder architecture that can be used in the system illustrated in FIG. 1.

FIG. 4 illustrates an example decoder architecture 400 for the decoder 112 illustrated in FIG. 1. The architecture 400 can receive or select a sample from the latent space. As illustrated in the example architecture 400 in FIG. 4, the latent space can be a 5 dimensional latent space. The architecture 400 can include a different neural network 402 for each sequence being recreated by the decoder 112. In the illustrated example, the decoder 112 is generating an in silico (or otherwise generating) a sequence that includes CDR1, CDR2, and CDR3. Accordingly, in the example illustrated in FIG. 4, the architecture 400 can include three neural networks, each of which corresponds to a respective on the CDR1, CDR2, or CDR3. The neural networks 402 can include dense layers or include long short-term recurrent neural network (LSTM-RNN) layers. Dense layers in the neural network can refer to layers that are non-linear. Dense layers can include a linear formula such as wx+b, but the end result of the dense layer can then be passed through a non-linear function referred to as an activation function as follows: $y=f(w*x+b)$. Example non-linear activation functions can include, for example, a unit step, sign, piece-wise linear, logistic, hyperbolic tangent, rectifier linear unit, or rectifier softplus. For example, the output of each of the neural networks 402 can be input into a feedforward layer 404 with a softmax activation. The output of the layer 404 can be a one-hot encoded matrix, which uses the same one-hot encoding as using in the encoder 108. The one-hot encoded output matrix can be converted into a sequence.

Once trained according the methods described herein, deep learning models can then be used to predict millions of antigen binders from a much larger in silico generated library of variants. These variants can be subjected to multiple developability filters, resulting in tens of thousands of optimized lead candidates. With its scalable throughput and capacity to interrogate across a vast protein sequence space, the methods described herein can be applied to a wide variety of applications that involve the engineering and optimization of antibody and other protein-based therapeutics.

EXAMPLES

Adaptive immunity can be driven by its ability to generate a highly diverse set of adaptive immune receptors (e.g., B and T cell receptors, as well as secreted antibodies) and the subsequent clonal selection and expansion of those receptors which are able to recognize foreign antigens. These principles can lead to unique and dynamic immune repertoires; deep sequencing can provide evidence for the presence of commonly shared receptors across individual organisms within one species. Convergent selection of specific receptors towards various antigens offers one explanation for the presence of commonly shared receptors across individual organisms. Convergent selection in antibody repertoires of mice can occur for a range of protein antigens and immunization conditions. In the present example, variational encoding was performed using a system similar to system and architectures illustrated in FIGS. 1-3, among others. The example uses a generative modelling technique that combines variational autoencoders with a mixture model, such as a Gaussian mixture model (GMM)-based clustering. The system, using variational encoding, can map antibody repertoires into a lower-dimensional latent space enabling us to discover a multitude of convergent, antigen-specific sequence patterns (AASP). Using a linear, one-versus-all support vector machine (SVM), the system identified sequence patterns that are predictive of antigenic exposure with an accuracy of up to 95%. Recombinant expression of both natural and variational encoding-generated antibodies possessing AASPs confirms binding to target antigen. This example illustrates that deep generative modelling can be applied for immunodiagnostics and antibody discovery and engineering.

I. Results

Targeted deep sequencing of the rearranged B cell receptor (BCR) locus can reveal the repertoire of B cells or expressed antibodies in a given tissue or cell population. Deep sequencing data was used to analyze the antibody repertoires in the bone marrow of 45 BALB/c mice, which were divided into cohorts immunized with protein antigens of either ovalbumin (OVA), hen egg lysozyme (HEL), blue carrier protein (BCP) or respiratory syncytial virus fusion protein (RSV-F). OVA, HEL and BCP cohorts were further subdivided into groups receiving zero, one, two or three booster immunizations, as illustrated in FIG. 2 and outlined in Table 1. Serum ELISAs confirmed antigen-specific antibody titers in all mice, with mice receiving only a primary immunization exhibiting significantly weaker titers. RNA was extracted in bulk from the bone marrow and variable heavy chain IgG sequencing libraries were prepared using a two-step RT-PCR protocol. Libraries were sequenced on Illumina's MiSeq, quality processed and aligned, yielding across all mice a total of 243'374 unique combinations of all three complementarity-determining regions (CDRs).

TABLE 1

| Immunization Schedules | | | | | | | | | |
|---|---|---|---|---|---|---|---|---|---|
| | | Primary | | 1st Boost | | 2nd Boost | | 3rd Boost | |
| Group | n | Antigen | Adjuvant | Antigen | Adjuvant | Antigen | Adjuvant | Antigen | Adjuvant |
| OVA, no boost | 3 | 200 µg OVA | 20 µg MPLA | | | | | | |
| OVA, 1 boost | 3 | 200 µg OVA | 20 µg MPLA | 50 µg OVA | | | | | |
| OVA, 2 boost | 3 | 200 µg OVA | 20 µg MPLA | 50 µg OVA | 20 µg MPLA | 50 µg OVA | | | |
| OVA, 3 boost | 3 | 200 µg OVA | 20 µg MPLA | 50 µg OVA | 20 µg MPLA | 50 µg OVA | 20 µg MPLA | 50 µg OVA | |
| HEL, no boost | 3 | 200 µg HEL | 20 µg MPLA | | | | | | |
| HEL, 1 boost | 3 | 200 µg HEL | 20 µg MPLA | 50 µg HEL | | | | | |
| HEL, 2 boost | 3 | 200 µg HEL | 20 µg MPLA | 50 µg HEL | 20 µg MPLA | 50 µg OVA | | | |
| HEL, 3 boost | 3 | 200 µg HEL | 20 µg MPLA | 50 µg HEL | 20 µg MPLA | 50 µg OVA | 20 µg MPLA | 50 µg OVA | |
| BCP, no boost | 3 | 200 µg BCP | 20 µg MPLA | | | | | | |
| BCP, 1 boost | 3 | 200 µg BCP | 20 µg MPLA | 50 µg BCP | | | | | |
| BCP, 2 boost | 3 | 200 µg BCP | 20 µg MPLA | 50 µg BCP | 20 µg MPLA | 50 µg OVA | | | |
| BCP, 3 boost | 3 | 200 µg BCP | 20 µg MPLA | 50 µg BCP | 20 µg MPLA | 50 µg OVA | 20 µg MPLA | 50 µg OVA | |
| RSV-F, 2 boost | | | | | | | | | |

Figure 6:
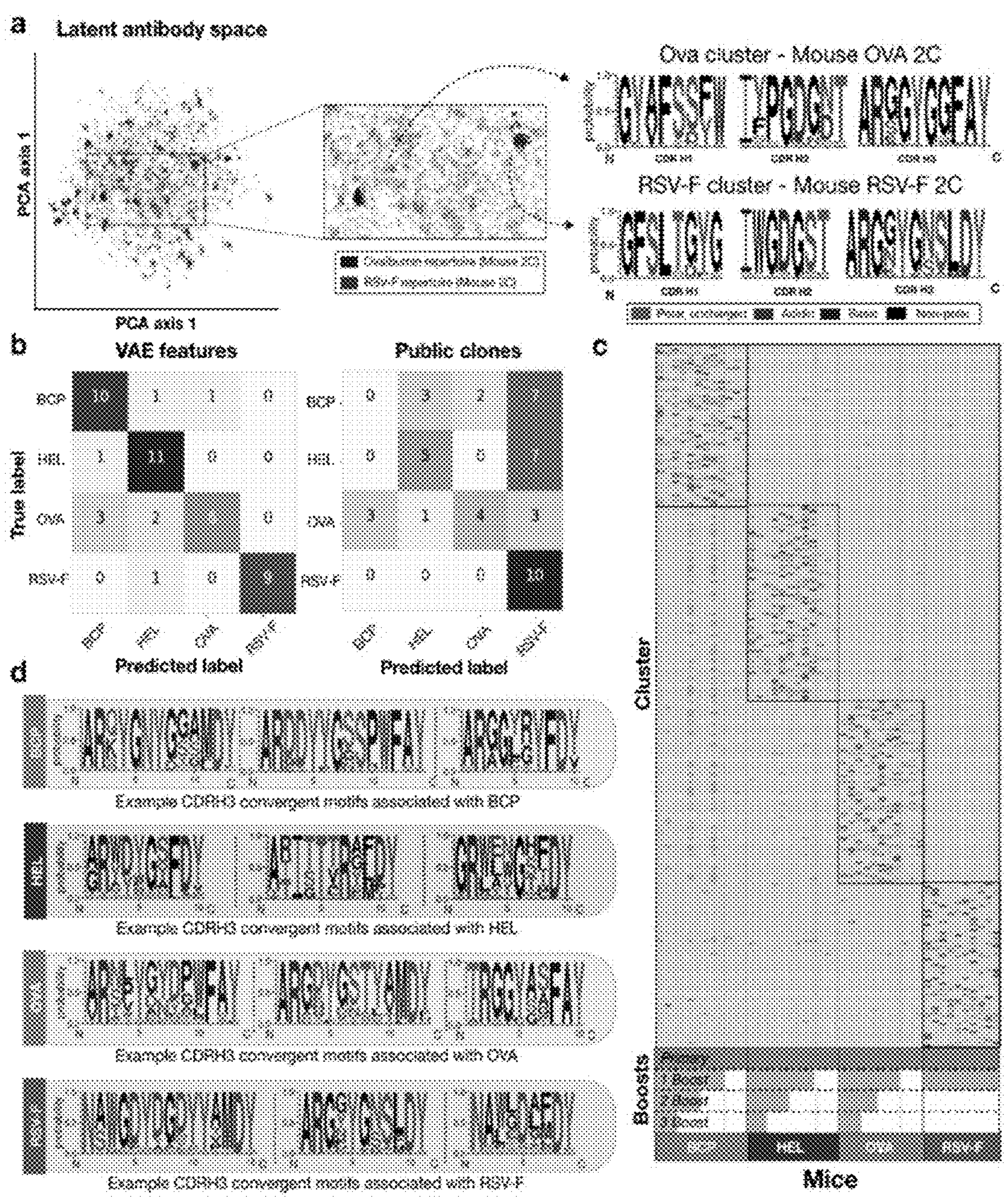
FIG. 6 illustrates an identification and characterization of antigen-associated sequences. (A) Ten-dimensional latent space of two antibody repertoires visualized by principal component analysis (PCA). Blue and red dots indicate sequences belonging to one OVA (2C) and RSV-F (2C) repertoire, respectively. Enlarged area highlights two learned clusters only containing sequences specific to one repertoire and their respective sequence motifs. (B) Antibody repertoires are transformed into vectors based on the learned sequence clusters in latent space. Recoded vectors are used as input for a linear support vector machine (SVM) classifier of antigen exposure. Confusion matrices show the aggregated prediction results of each model during 5-fold cross-validation using the cluster labels and raw sequences as features. (C) Heatmap contains all predictive and convergent sequence clusters for each cohort. Dashed red line indicates mice that only received the primary immunization. (D) Example sequence logos of convergent clusters found in each antigen cohort.

FIG. 6 illustrates the workflow to evaluate to which extent convergence occurs that is beyond exact sequence similarity. FIG. 6 illustrates an identification and characterization of antigen-associated sequences. (A) Ten-dimensional latent space of two antibody repertoires visualized by principal component analysis (PCA). Blue and red dots indicate sequences belonging to one OVA (2C) and RSV-F (2C) repertoire, respectively. Enlarged area highlights two learned clusters only containing sequences specific to one repertoire and their respective sequence motifs. (B), Antibody repertoires are transformed into vectors based on the learned sequence clusters in latent space. Recoded vectors are used as input for a linear support vector machine (SVM) classifier of antigen exposure. Confusion matrices show the aggregated prediction results of each model during 5-fold cross-validation using the cluster labels and raw sequences as features. (C), Heatmap contains all predictive and convergent sequence clusters for each cohort. Dashed red line indicates mice that only received the primary immunization. (D), Example sequence logos of convergent clusters found in each antigen cohort.

Figure 7:
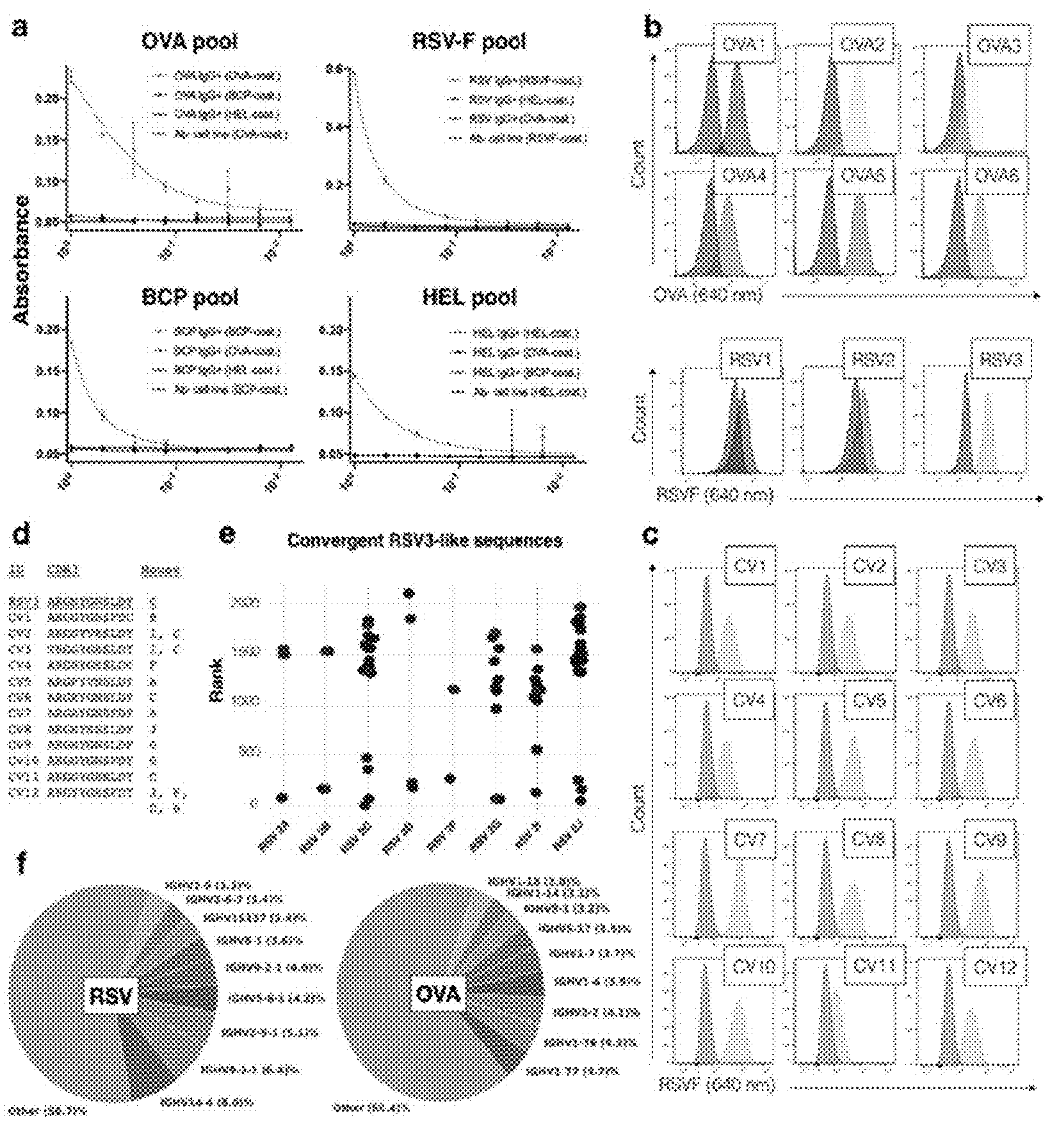
FIG. 7 illustrates cluster specific sequences across various repertoires containing antigen-specific antibodies. (A) Dose-dependent absorbance curves of supernatant prepared from the four antigen-associated heavy-chain pools against every antigen. (B) Flow cytometry histograms of six monoclonal cell populations each utilizing a different convergent OVA-associated or RSV-F associated $V_H$. Grey histograms represent negative controls, colored histograms show the convergent antibodies. (C) Flow cytometry histograms of 12 monoclonal cell populations of convergent variants (CV), which use a different $V_H$ sequence from the same cluster as RSV3. (D) Table shows the CDRH3s of the selected CVs and the RSV-F immunized mouse repertoire in which they were found. Red letters indicate differences to the initially discovered sequence RSV3 sequence. Figure discloses SEQ ID NOS 53-65, respectively, in order of appearance. (E) Scatterplot shows the frequency-rank distributions per mouse repertoire of CVs from RSV3 cluster. Red dots highlight $V_H$ confirmed to be binding in (C). (F) Pie charts show the nine most utilized V-gene germlines in convergent clones for both RSV-F and OVA.

FIG. 7 illustrates cluster specific sequences across various repertoires. (A), Dose-dependent absorbance curves of supernatant prepared from hybridoma cells expressing antibodies with convergent variable heavy (VH) chain pools for each antigen. (B), Flow cytometry histograms of six monoclonal cell populations each utilizing a different convergent OVA-associated or RSV-F associated VH. Grey histograms represent negative controls, colored histograms show the convergent antibodies. (C), Flow cytometry histograms of 12 monoclonal cell populations of convergent variants (CV), which use a different VH sequence from the same cluster as RSV3. (D), Table shows the CDRH3s of the selected CVs and the RSV-F immunized mouse repertoire in which they were found. Red letters indicate differences to the initially discovered sequence RSV3 sequence. (E), Scatterplot shows the frequency-rank distributions per mouse repertoire of CVs from RSV3 cluster. Red dots highlight VH confirmed to be binding in c. (F), Pie charts show the nine most utilized V-gene germlines in convergent clones for both RSV-F and OVA.

Figure 14:
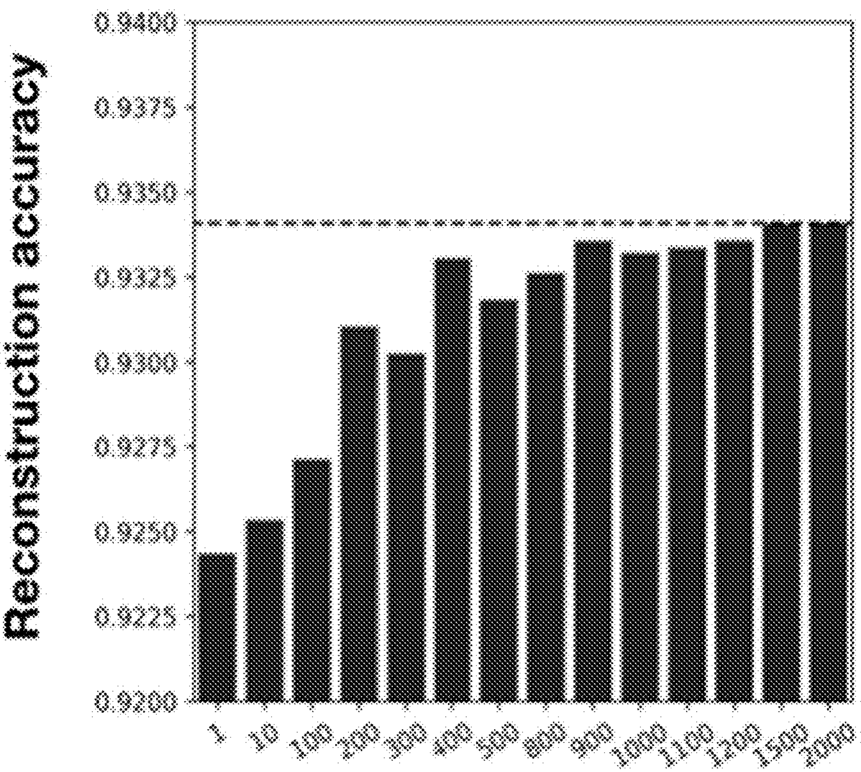
FIG. 14 illustrates reconstruction accuracy of a variational autoencoder. Bar plots show the achieved reconstruction accuracy as a function of the number of clusters. Increasing the of amount clusters (k) results in an increase in the reconstruction accuracy, with diminishing returns after k=2000.

The system and architectures illustrated in FIGS. 1-5, among others, can encode and decode CDR1, CDR2, CDR3 sequences and their appropriate combinations to and from the latent space. The sequences in the latent space can be clustered according to a GMM, with similar sequences falling into the same cluster and closely related clusters occupying similar regions in the latent space. In some embodiments, deep neural networks are used to encode (FIG. 3) And decode (FIG. 4) sequences and are optimized with respect to the GMM prior and their ability to reconstruct the input sequences. Increasing the dimensionality of the latent encoding improved the reconstruction ability of the model and by using a ten-dimensional encoding layer the system achieved reconstruction accuracies over 93% (FIG. 14). As illustrated in FIG. 6A, principal component analysis (PCA) can be used to visualize the latent encodings to show that related sequences indeed mapped to the same cluster and areas in latent sequence space. The amount of convergence was quantified by identifying latent clusters that were highly predictive for the respective antigen immunization. Sequences were grouped into their respective clusters and the re-coded repertoires were used to train and cross-validate a linear, one-versus-all SVM classifier. In order to establish a baseline for this workflow, a linear support-vector machine (SVM) was also trained on the occurrence of public clones (exact CDRH1-CDRH2-CDRH3 a.a. sequence matches), which yielded an accuracy of 42% for prediction of antigen exposure (5-fold cross-validation). In contrast, when using VAE-based cluster assignments and subsequently encoding repertoires based on cluster enrichment, the resulting classifiers were able to achieve a prediction accuracy of over 80% (FIG. 6B). The models were retrained on the complete data and the clusters were selected based on a non-parametric permutation tests and significantly enriched clusters with a Bonferroni corrected p-values below 0.05 were selected. Closer inspection reveals that not every mouse expressed all of their respective convergent clusters, but rather a smaller, yet still predictive subset (FIG. 6C). The number of convergent clusters discovered correlated well with antigen size and complexity. By comparing all the sequences mapping into a given cluster, the system demonstrated how VaDE is able to build biological meaningful clusters. Again, comparing aggregated sequence logos to logos generated from single repertoires shows the potential diversity of the convergent sequence space and highlights that convergence is not focused on specific CDRs (FIG. 6A and FIG. 6C).

Figure 9:
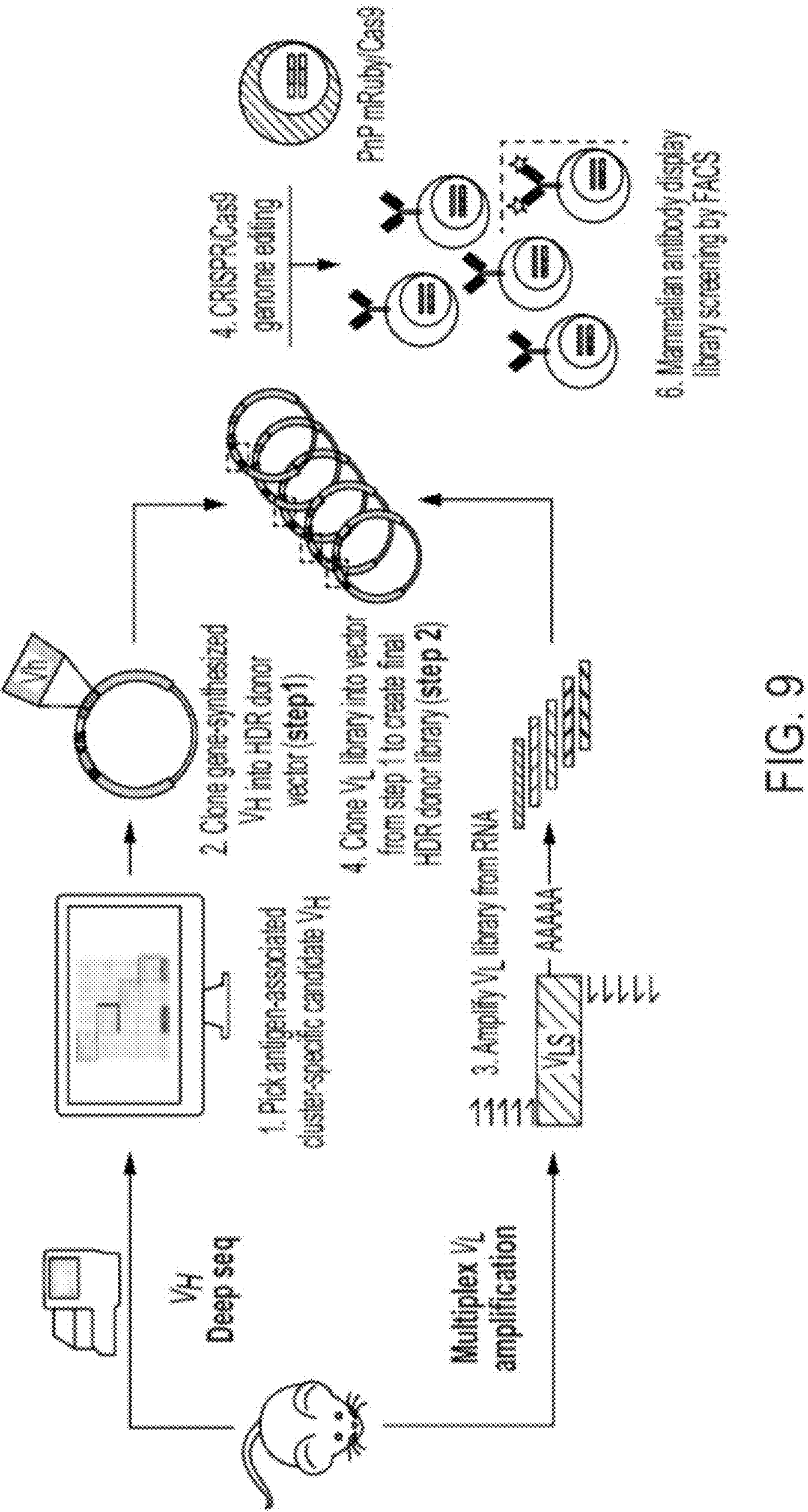
FIG. 9 illustrates an exemplary work flow for generating and testing new $V_H$ sequences selected by the deep generative models provided. Candidate heavy chains are picked from the bulk heavy-chain sequencing dataset for each antigen based on the implemented bioinformatic sequence clustering framework. Sequences are gene-synthesized and cloned into the HDR donor vector (step 1). For each antigen, the light-chain repertoire is amplified from the RNA of a mouse that was immunized with the same antigen by multiplex PCR. The resulting light-chain library is then cloned into the HDR donor vector created in step 1 in order to create a separate HDR donor VL library for each heavy chain (step 2). The resulting HDR donor libraries are then used to act as DNA repair template for CRISPR/Cas9 based integration into the PnP mRuby/Cas9 cells thereby creating a library of hybridoma cell clones that express antibodies with the same candidate heavy chain but different light chains. Antigen-specific clones are enriched by fluorescence-activated cell sorting.
Figure 10:
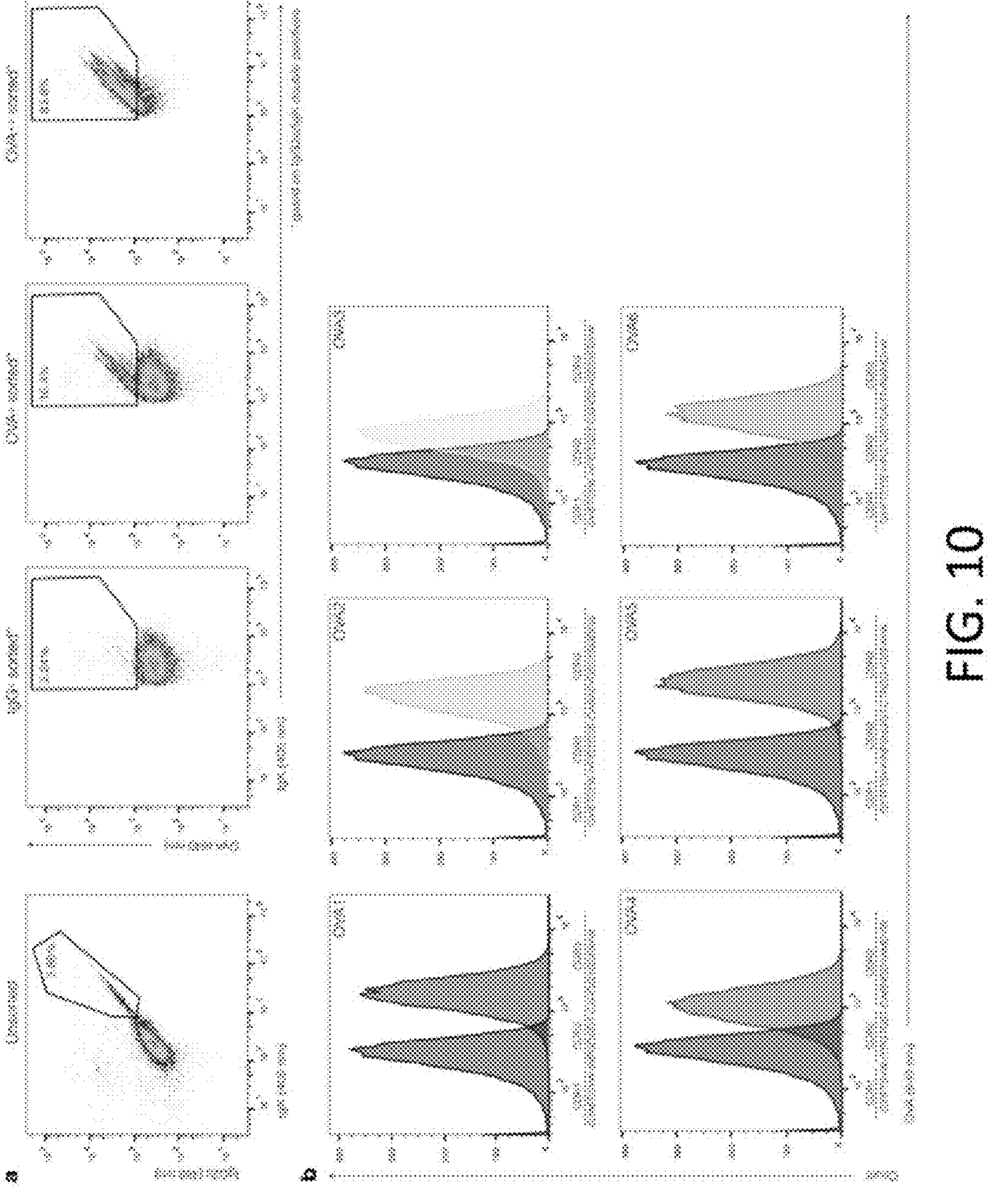
FIG. 10 illustrates flow cytometry analysis of hybridoma libraries. Flow cytometry analysis of hybridoma cell libraries for (A)-(B), OVA and (C)-(D) RSV-F. Sequential library enrichment dot plots are shown in (A) and (C). Respective antigen-specific monoclonal cell lines are shown in histogram plots (B) and (D) with respect to a negative control cell line that is not-specific for the given antigen.
Figure 10:
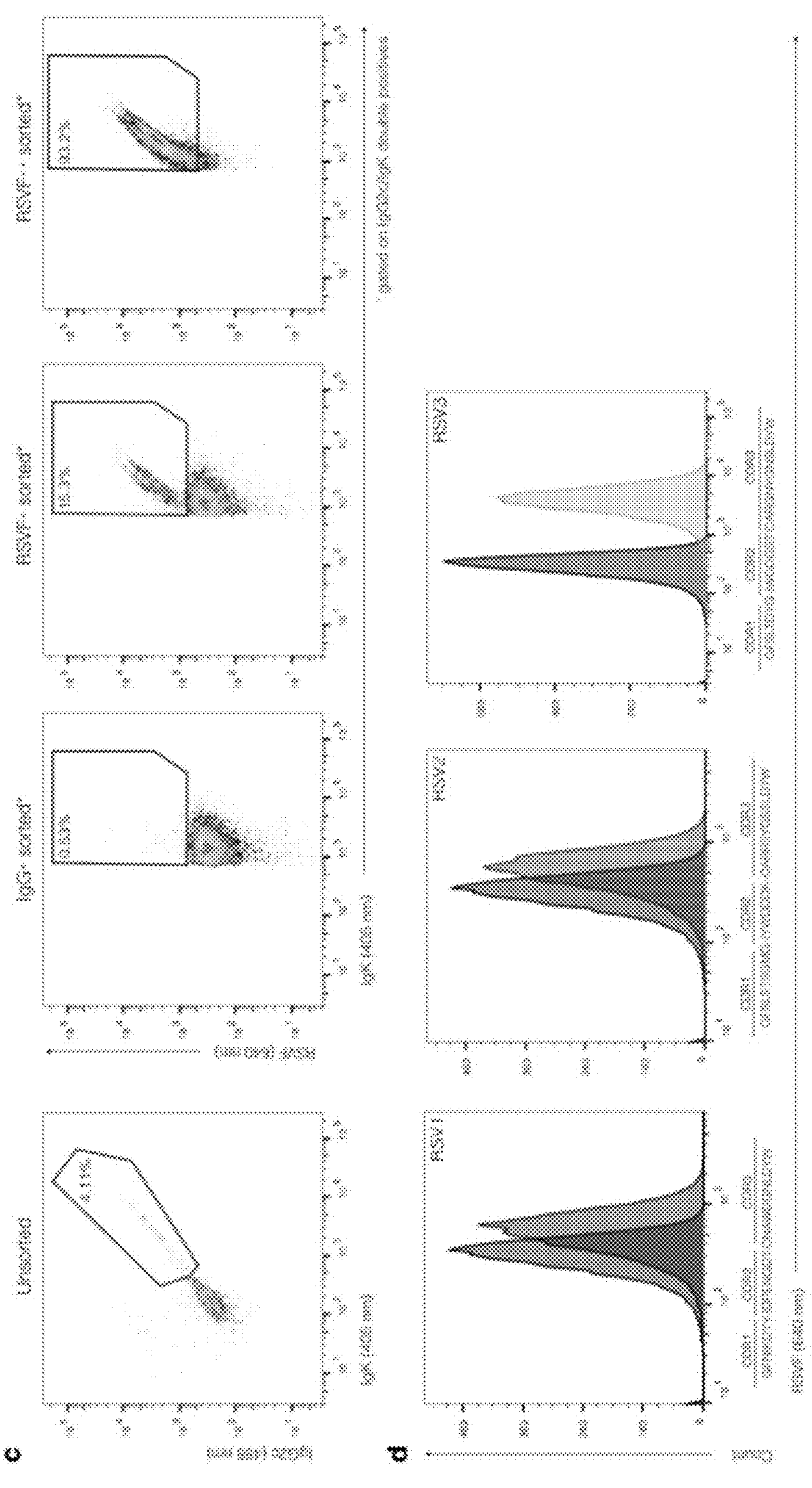
Figure 11:
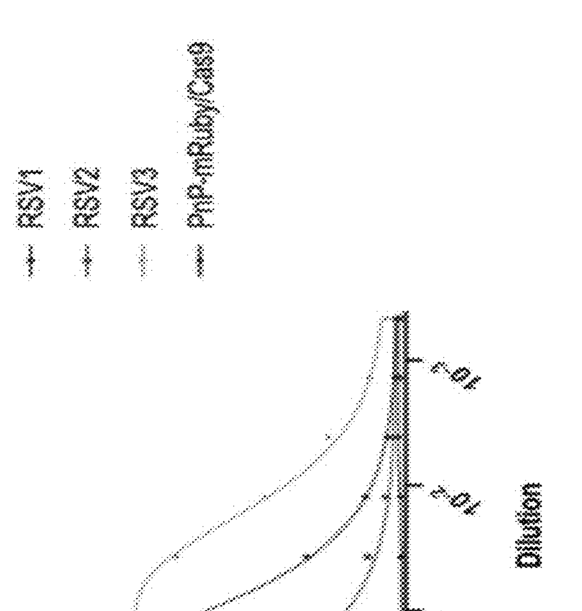
FIG. 11 illustrates ELISA data of convergent sequences confirmed to be antigen-specific. Supernatant ELISA profiles of antigen-specific hybridoma monoclonal cell lines are shown for (A) OVA and (B) RSV-F. Starting cell line PnP-mRuby/Cas9 was used as negative control.
Figure 11:
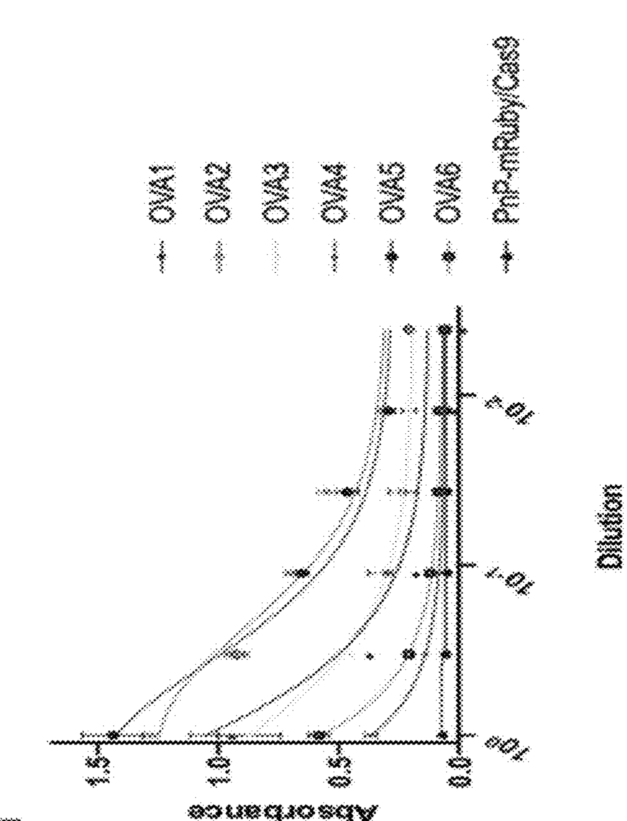
Figure 12:
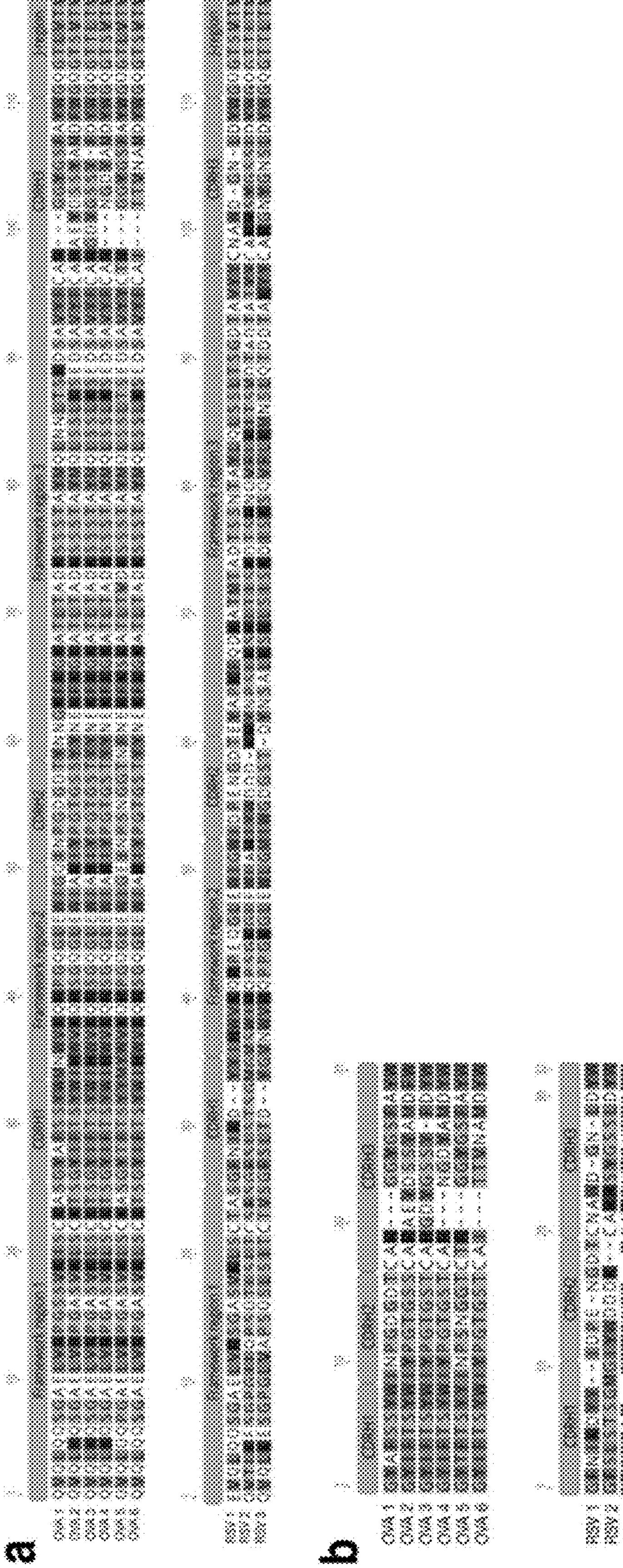
FIG. 12 illustrates alignments of convergent sequences confirmed to be antigen-specific. $V_H$ amino acid alignments for antigen-specific antibodies. (A) Full-length VDJ-alignments are shown for OVA and RSV variants (SEQ ID NOS 96-104, respectively, in order of appearance). (B) Concatenated CDRH1-CDRH2-CDRH3 amino acid alignments for OVA and RSV-F are shown (CDR sequences are not intended to be interpreted as consecutive). Color-code used is derived from the Clustal coloring scheme with software Geneious V 10.2.6. Figure discloses the CDR sequences as SEQ ID NOS 76-81, 79, 82-83, 79, 82, 84, 47-48, 85, 79, 82, and 86-95, respectively, in order of appearance.

In order to confirm that antigen-predictive sequence convergence is indeed driven by antigen recognition, a small subset of convergent $V_H$ sequences were expressed together with a variable light chain ($V_L$) library cloned from single repertoires (FIGS. 19-22 and FIG. 9). A mammalian expression system was utilized for display and secretion of antibodies through coupling to CRISPR-Ca9-mediated library integration to screen for antigen specificity. ELISAs performed on the supernatant of our library cell lines demonstrated correct specificity for all four antigens (FIG. 6A, FIG. 6C). Fluorescence-activated cell sorting (FACS) further identified single antigen-specific clones (FIG. 7B, FIG. 9, and FIG. 10). We then proceeded to more closely investigate the heavy-chain pools of two antigens, RSV-F and OVA, through single clone isolation by fluorescence-activated cell sorting (FACS). Antigen-specific clones and their corresponding heavy chains identified in this step were confirmed by ELISA, which again was performed on the supernatant of the now monoclonal cell populations (FIG. 7B, FIG. 7C, and FIG. 10). This procedure allowed us to confirm antigen specificity of 6 (out of 6 selected) OVA and 3 (out of 4 selected) RSV-F convergent VH sequences (FIGS. 19-22). VH chains were able to pair with VL chains from a different mouse repertoire, additionally highlighting convergence with respect to VH chain-dominated binding (FIGS. 19-22). While all antigens were associated with a variety of V-gene germlines, we noticed that convergent antibodies were utilizing different V-gene segments in an antigen-dependent manner, highlighting that the original V-gene germline contributes to convergent selection (FIG. 7F).

Figure 13:
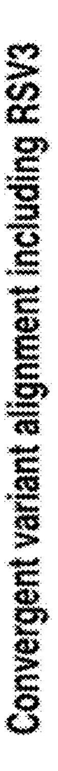
FIG. 13 illustrates an amino acid sequence alignment of convergent variants from RSV3 cluster (SEQ ID NOS 105-116 and 104, respectively, in order of appearance). $V_H$ amino acid alignments for convergent natural variants (NV) from RSV3 cluster. Color- code used is derived from the Clustal coloring scheme with Geneious V 10.2.6
Figure 13:
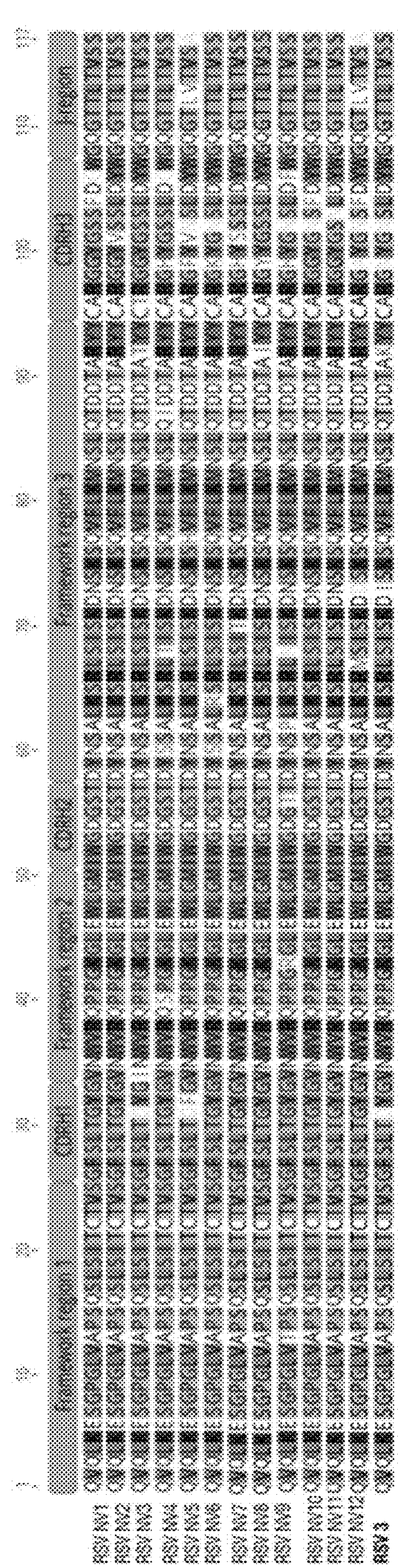

In order to confirm that antibody sequence variants mapping to the same convergent cluster were also antigen-specific, we recombinantly expressed 12 convergent $V_H$ variants (derived from other mice immunized with the same antigen) from the cluster mapping to one of the confirmed RSV-F binders (RSV3, FIG. 13). These 12 convergent variants were expressed with the same $V_L$ of RSV3. Flow cytometry confirmed that all 12 of these convergent variants were indeed antigen-specific (FIG. 7*c*). Using standard clonotype definitions of 100% or 80% $V_H$ CDRH3 a.a. identity (2, 4), only zero or five of the 12 variants, respectively, would have been identified as convergent across repertoires (FIG. 7*d*). In contrast, the VAE model was able to discover variants of RSV3 with as low as 64% CDRH3 a.a. identity (4 out of 11 mismatches), verifying the large potential diversity revealed by the previous logo plots (FIG. 6*d*, FIG. 7*f*). Besides their sequence diversity, these clones also confirmed the large abundance range with confirmed binders being of high, medium and low frequencies in their respective mouse repertoires (FIG. 7*e*).

Figure 15:
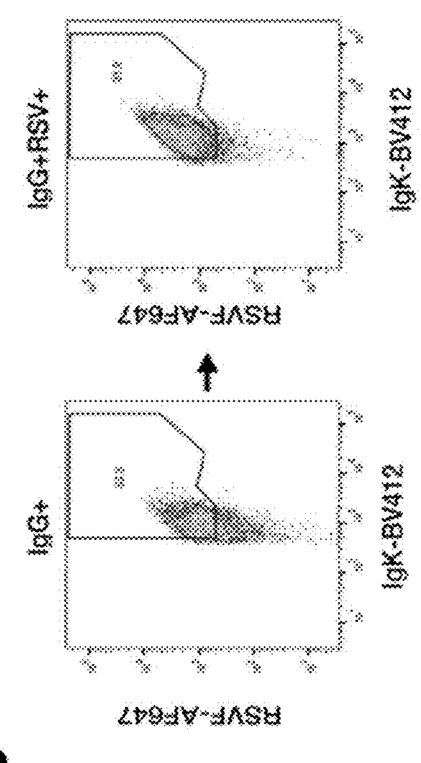
FIG. 15 illustrates a workflow for RSV3 CDRH3 antibody library screening workflow. (A) RSV3 CDR113 libraries were generated by CRISPR-Cas9 homology directed mutagenesis using an ssODN with degenerate codons representing a sequence space depicted by the logo shown. (B) Transfected cells were subsequently sorted in two consecutive steps for antibody expression and specificity or negativity towards RSV-F.
Figure 15:
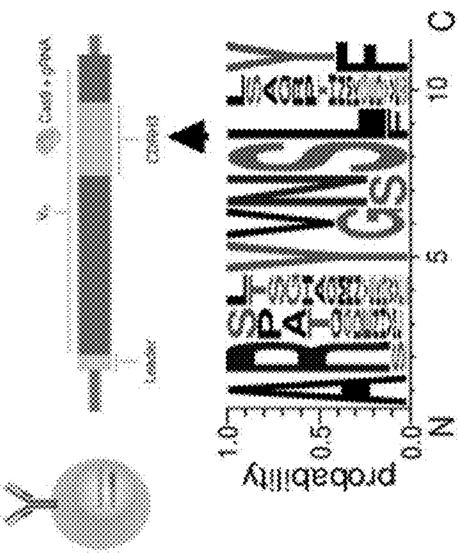
Figure 16:
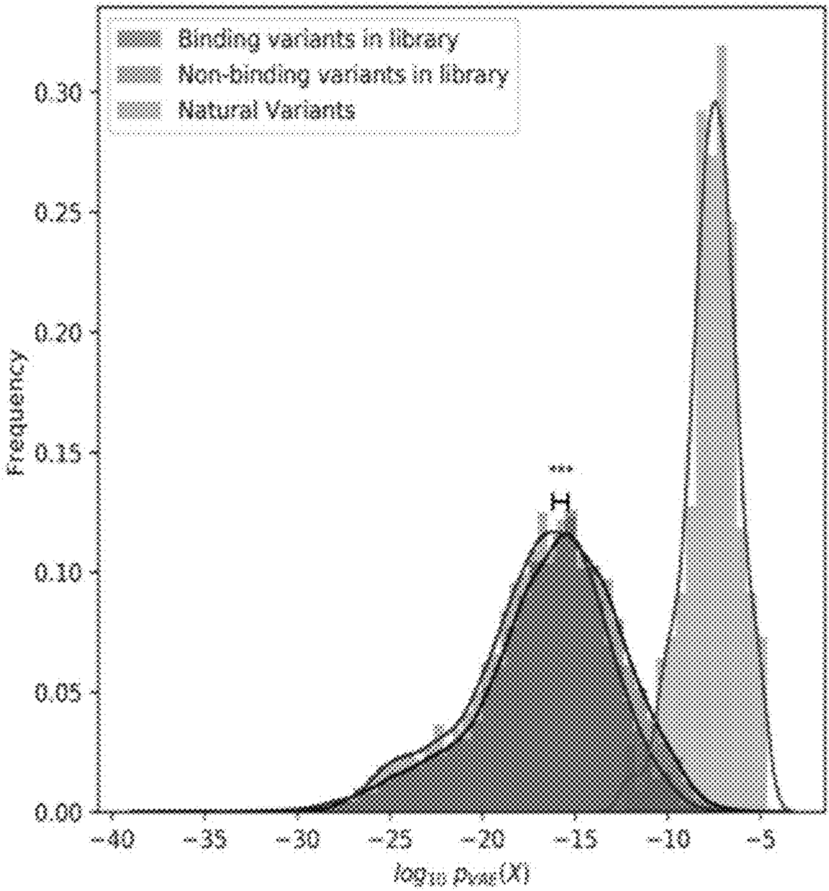
FIG. 16 illustrates sampling results from an RSV3 generated CDRH3 library. Histograms show how likely sequences from the positive (blue) and negative (red) fraction of the RSV3 CDRH3 library screen are to occur according to the VAE decoder model. Positive variants are slightly but significantly ($P<0.001$, Mann-Whitney U test) more likely to occur. The green histogram to the right depicts the probabilities of the variants observed in the biological repertoires.
Figure 17:
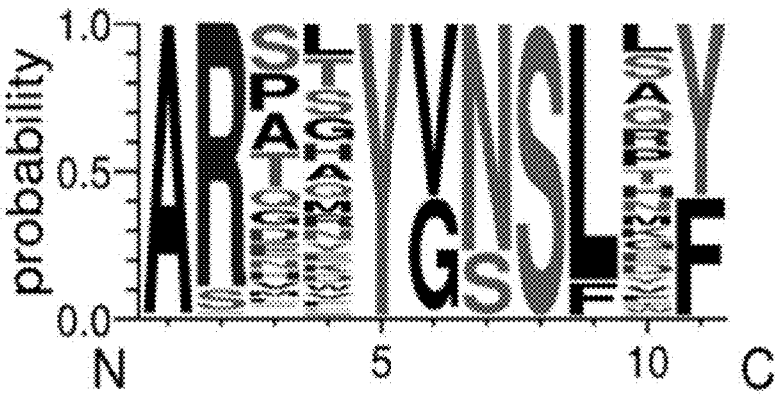
FIG. 17 illustrates deep sequencing results from RSV3 CDRH3 library screening. Sequence logos show the aggregated sequences found in the (A) positive and (B) negative fractions of the RSV3 CDRH3 library screen.
Figure 17:
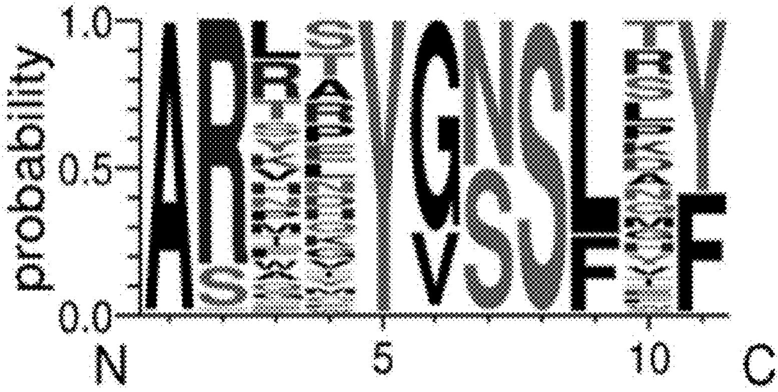

Finally, we aimed to understand how well the VAE model is able to generalize to unseen data. To start, we experimentally produced an antibody CDRH3 library of the RSV3 clone through CRISPR-Cas9 homology-directed mutagenesis; while the diversity of the library was designed to model decoder-generated sequences of the RSV3 cluster, it also contained fully randomized positions (FIG. 15*a*). Screening of the hybridoma antibody library by FACS followed by deep sequencing yielded 19,270 surface-expressed variants of whom 7,470 were confirmed to be antigen-binding (FIG. 15*b*). When assessing the probabilities of these novel variants under the VAE model, we found that binding CDRH3s were significantly more likely to be generated than non-binding variants (FIG. 16). However, since the library also contained a.a. that were not observed in nature, most of its variants were less likely to be generated by our model than naturally occurring sequences (FIGS. 16, 17). Yet, the overlap between the distributions indicated that the VAE model should have been able to generate some of these variants in silico. We confirmed this fact by sampling one million latent encodings.

II. Discussion

The present solution can reveal wide-scale convergence and provides an analysis tool and workflow for generating in silico sequences. The system can include a $V_H$ screening workflow that can combine bioinformatics and screening techniques based on an antibody expression and display system. Convergent clusters revealed by the encoder or in silico sequences generated by the decoder can be used to assess for optimal properties for drug development (e.g., antibody developability). Convergent cluster antibodies can also be used through experimental assays to identify their cognate binding epitope (e.g., peptide/protein antigen library arrays, mass spectrometry), these cognate epitopes may serve as targets for drug development. Convergent clusters may also be used as a diagnostic to assess the immune status or health/disease-state of an individual.

In summary, the system shows that wide-scale convergence across a range of antigens occurs in the antibody repertoire of mice. Current approaches used to detect convergence, such as looking at exact CDR3 sequence identity or using thresholds of 80% sequence identity, are only partly able to recover the full-scale of convergent patterns as we find dissimilarities greater than 40% in individual, convergent motifs. Other clustering algorithms, that might be employed to extract convergence, often also require the definition of an arbitrary similarity threshold. The present solution learns these parameters from the data, forming clusters of varying degrees of similarity. Additionally, they system can discover convergent motifs buried deep in the repertoire, highlighting the possibility that—as the amount available sequencing data increases—similar phenomena might be more commonly observed in humans as well. We furthermore show for the first time how deep generative modelling can be used to generate novel and functional antibodies in-silico, thereby drastically expanding antibody discovery capabilities from deep sequencing.

III. Methods

A. Immunizations

Female BALB/c mice (Charles Rivers) of 6-8 weeks old were separated into cohorts (10-12 mice) based on antigen: hen egg lysozyme (HEL), ovalbumin (OVA), blue carrier protein (BCP) and respiratory syncytial virus glycoprotein (RSV). Mice were immunized with subcutaneous injections of 200 µg antigen and 20 µg monophosphoryl lipid A (MPLA) adjuvant. The final immunizations (boost 1, 2 or 3) were done with 50 µg antigen per intraperitoneal injection without any adjuvants. The middle immunizations (boost 1 and/or 2) were done with 50 µg antigen and 20 µg MPLA. Sequential injections were interspaced by three weeks. All adjuvants and antigens were prepared and aliquoted before the experiments and mixed on the days of the corresponding injection. Mice were sacrificed 10 days after their final immunization and bone marrow was extracted from femurs of hindlegs. The isolated bone marrow was then centrifuged at 400 g at 4° C. for 5 minutes. The supernatant was removed and 1.25 mL of Trizol was added. The bone marrow was then homogenized using a 18G×2 inch needle (1.2×50 mm). I mL of the resulting Trizol solution was then frozen at −80° C. until processing. Mouse cohorts and immunization groups are described in Table 1.

B. RNA Extraction from Murine Bone Marrow 1 mL of the homogenate was used as input for the PureLink RNA Mini Kit (Life Technologies, 12183018A). RNA extraction was then conducted according to the manufacturer's guidelines.

C. Antibody Repertoire Library Preparation and Deep Sequencing

Antibody variable heavy chain ($V_H$) libraries for deep sequencing were prepared using a protocol of molecular amplification fingerprinting (MAF), which enables comprehensive error and bias correction (Khan, T. A., et al., Accurate and predictive antibody repertoire profiling by molecular amplification fingerprinting. Sci Adv, 2016. 2(3): p. e1501371). Briefly, a first step of reverse transcription was performed on total RNA using a gene-specific primer corresponding to constant heavy region 1 (CH1) of IgG subtypes and with an overhang region containing a reverse unique molecular identifier (RID). Next, multiplex PCR is performed on first-strand cDNA using a forward primer set that anneals to framework 1 (FR1) regions of $V_H$ and has an overhang region of forward molecular identifier (FID) and partial Illumina adapter; reverse primer also contains a partial Illumina sequencing adapter. A final singleplex PCR step is performed to complete the addition of full Illumina adapters. After library preparation, overall library quality and concentration was determined on the Fragment Analyzer (Agilent). Libraries were then pooled and sequenced on an Illumina MiSeq using the reagent v3 kit (2×300 bp) with 10% PhiX DNA added for quality purposes.

D. Data Pre-Processing and Sequence Alignment

Before alignment, the raw FASTQ files were processed by a custom CLC Genomics Workbench 10 script. Firstly, low quality nucleotides were removed using the quality trimming option with a quality limit of 0.05. Afterwards, forward and reverse read pairs were merged and resulting amplicons between 350 and 600 base pairs were kept for further analysis. Pre-processed sequences were then error-corrected and aligned.

E. Variational Deep Embedding (Vade) on Antibody Repertoires

Also referring to FIGS. 1 and 3, among others, following error and bias correction and alignment of antibody repertoire sequencing data, all discovered combinations of CDRH1, CDRH2 and CDRH3 for each dataset were extracted. In order to process CDRHs of various lengths, sequences were padded with dashes until a certain fixed length (maximum length for each CDRH in the data) was reached, as described above in relation to FIG. 3. Padded sequences were one-hot encoded, concatenated and used as input into the variational autoencoder (VAE) in relation to FIG. 3, among others. The VAE model jointly optimizes the ability to reconstruct its input together with a Gaussian mixture model (GMM)-based clustering of the latent space according to the following formula:

$$\mathcal{L}_{ELBO}(x) = \mathbb{E}_{q(y,z|x)}[\ln(x, y, z) - \ln q(y, z \mid x)]$$

With:

$$p(x, z, y) = p(c)p(z \mid y)p(x \mid z)$$
$$p(y) \sim Cat(\pi)$$
$$p(z \mid y) \sim \mathcal{N}(\mu_y, \sigma_y^2 \mathbb{I}_D)$$

And the following variational approximation of the posterior, where q(z|x, y) is assumed to be distributed according to a gaussian distribution:

$$q(y,z|x)=q(y|x)q(z|x,y)$$

Figure 5:
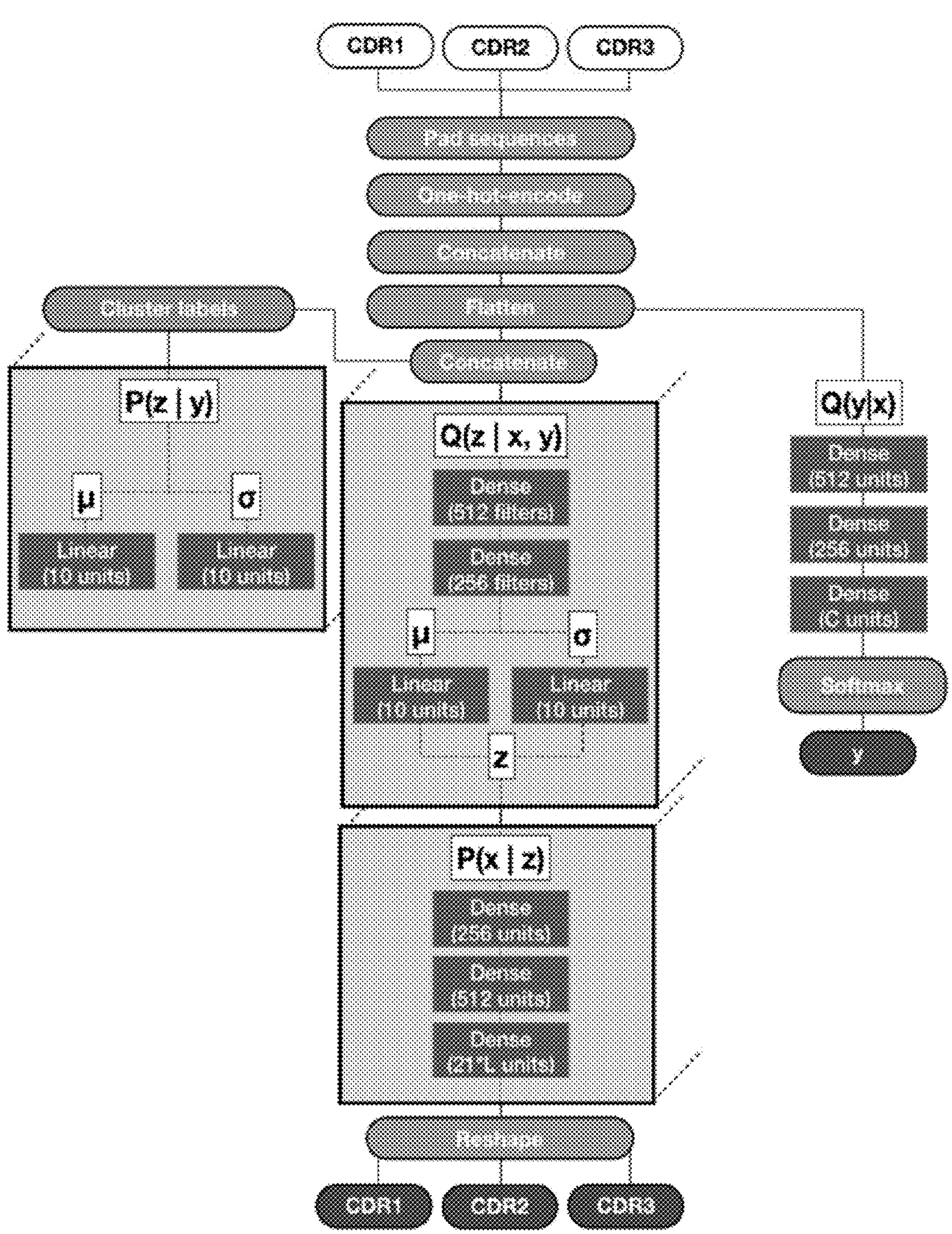
FIG. 5 illustrates an exemplary deep neutral network of a variational autoencoder. Grey boxes indicate the input into the model, while light red boxes indicate various (mathematical) operations. Purple boxes highlight the trainable layers of the model. Dark red indicates the output of the model. Grey boxes contain layers whose weights are shared across all cluster dimensions. The variational autoencoder can receive, as input, CDR1, CDR2, and CDR3. In order to process CDRHs of various lengths, the system pads the sequences with dashes until a certain fixed length (maximum length for each CDRH in the data) was reached. The system one-hot encodes the padded sequences, concatenates and uses this as input into the variational autoencoder (VAE).

This technique may not perform a mean field approximation when modelling the posterior, thereby increasing model stability. The system can encode and decode every input sequence as if the sequence would belong to every cluster (indicated through a one-hot encoded cluster label) using shared weights in every layer. The system then weights the final contributions to the overall loss by the separately predicted probabilities q(y|x), which describe the probability of a sequence belonging to a specific cluster (FIG. 5). The decoder maps input sequences and concatenated class label into a lower dimensional (d=10) space using two dense layer with rectified linear unit (ReLU) activation followed by the final 10-dimensional layer. Sequences are sampled and recreated from the latent space using the decoder. The decoding network (FIG. 5) employs two separate dense layers with ReLU activation followed by a dense layer with a linear activation, whose output can be reshaped and normalized with a softmax activation in order to reconstruct the probabilities of the initial, one-hot encoded CDRHs. The standard categorical cross-entropy loss can be used as the reconstruction term. For example, every VAE model can be trained on a single GPU node of a parallel computing cluster (e.g., the ETH Zurich parallel computing cluster). Training can include 200 epochs for all models using a stochastic optimization algorithm.

VaDE can jointly optimize a deep generative model together with a Gaussian mixture model (GMM)-based clustering of the latent space as illustrated in FIG. 2. The encoder 108 concatenates CDR1, CDR2 and CDR3 sequences and feeds them to a self-attention layer. Input and output of this layer form a residual block, which is normalized. The normalized residual block is input into a position-wise, fully-connected feedforward neural network layer. The output of this layer is then mapped into the lower-dimensional latent space using a linear transformation.

Also referring to FIGS. 1 and 4, among others, the decoder 112 can recreate sequences from the latent space. The decoder 112, as illustrated in FIG. 4, can employ three separate long short-term recurrent neural network (LSTM-RNN) layers, whose output is processed using a feedforward layer with a softmax activation in order to individually reconstruct the initial, one-hot encoded CDRs. Every VaDE model was trained on a GPU node of a parallel computing cluster, for example. Training can include 100 or more epochs of pre-training, followed by 1000 epochs of full training. For pre-training a deep autoencoder model, whose layers mirror the above described architecture illustrated in FIG. 3, was used. After pre-training was completed, a GMM was learned on the latent space and both the layer weights of the autoencoder and the GMM parameters were used to initialize the full model.

F. Predicting Antigen Exposure of Single Antibody Repertoires

Repertoire datasets were split into five folds with each fold being approximately balanced in the number of distinct antigen groups and each dataset appearing only once across all folds. This split was then used to perform a cross-validation procedure in which each of the five folds were set aside as a test set once and the remaining four folds were used as training data. For each of the five training/test splits a separate VAE model was learned by combining all sequences across all repertoires from the training set as input. Clustering assignments or sequences from both the training and the test set were then calculated for the trained model. Based on these cluster labels each repertoire was recoded as an n-dimensional vector, where n is the number of possible clusters and the i-th element indicates the number of sequences mapping to the i-th cluster in the given repertoire. These vectors were then used to train and validate linear support vector machines (SVM) in a one-versus-all setting. In order to prevent a more resource-intensive nested cross-validation procedure we decided to not optimize the hyperparameters of the SVMs and instead chose to use the standard values given by scikit-learn's 'SVC' implementation (using a linear kernel). For visualization purposes the results of each cross-validation step were grouped together in one single confusion-matrix (FIG. 6B).

G. Identification of Antigen-Associated Sequence Clusters

In order to identify antigen-associated sequence clusters from antibody repertoires, we performed non-parametric permutation test in order to determine whether sequence reads were specifically enriched in one cluster given a specific cohort (FIG. 6D). In order to account for multiple testing, Bonferroni correction was applied to all p-values in each cohort. We proceeded by randomly choosing one CDR1-CDR2-CDR3 combination and its cognate full-length variable region from each cluster for further validation.

H. Generation of Cluster-Specific, in Silico Variants

Figure 8:
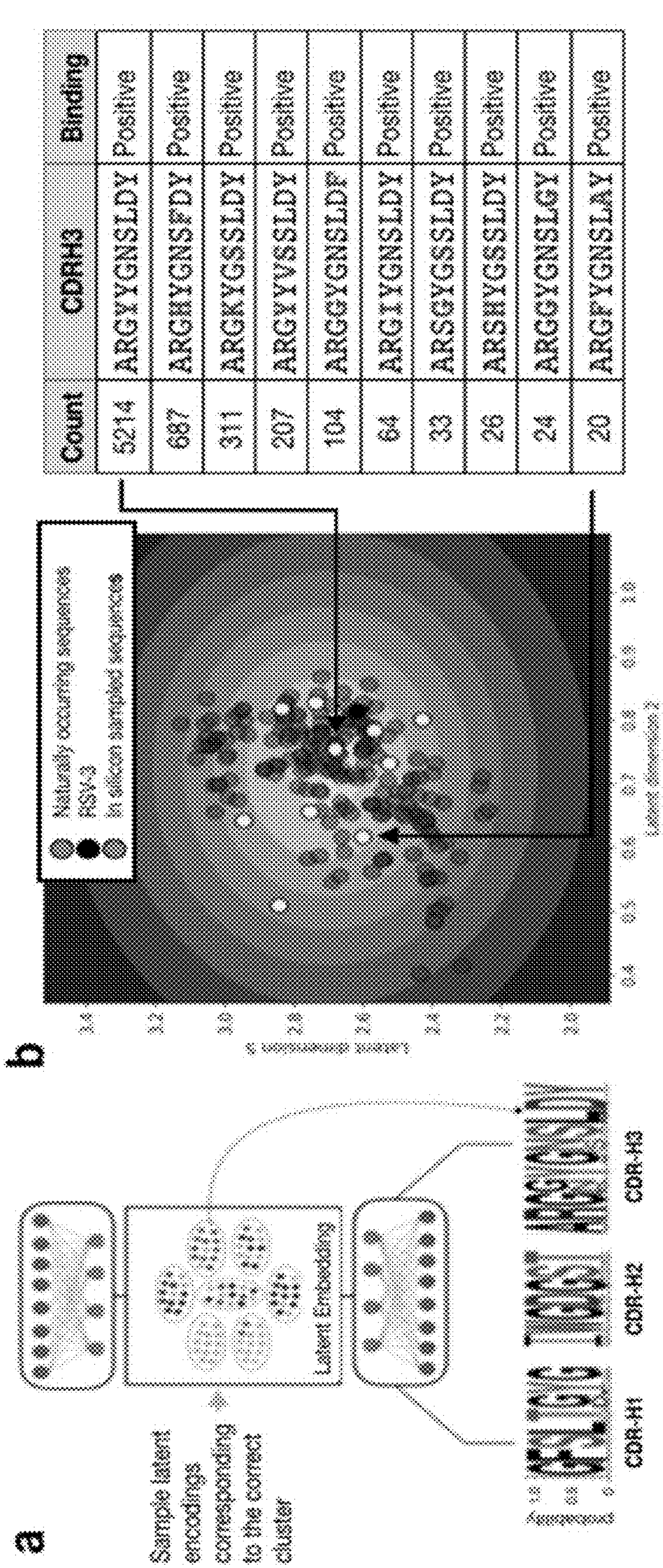
FIG. 8 illustrates deep generative modelling and in silico antibody sequence generation. (A) Schematic deep generative modeling of antibody sequence space: a cluster is either chosen or randomly sampled and based on the parameters chosen, a random sample is drawn from a multivariate normal distribution. The encoder then translates the encoding into a multivariate multinomial distribution from which a novel sequence is sampled. (B) Scatter plot shows the two latent naturally occurring variants, yellow dots show the ten most frequently in-silico sampled encodings that were confirmed to be binding antibodies. The table on the right shows their CDRH3 sequence and its count after 1,000,000 samples (SEQ ID NOS 65-75, respectively, in order of appearance). Red letters indicate differences to the initial biological sequence (RSV3, shown in black).

Cluster-specific, novel variants were generated in silico by sampling data points in the latent space from a multi-variate Gaussian distribution, where parameters were given by the respective cluster parameters from the final VAE model. These sampled data points were then fed into the decoding network resulting in position probability matrices for each CDRH (see FIG. 8A). For each data point a given CDRH1, CDRH2 and CDRH3 was generated. This process was repeated for a million iterations. The log probability of single sequences was approximated by taking the average of 500 samples of the evidence lower bound (ELBO).

I. Hybridoma Cell Culture Conditions

All hybridoma cell lines and libraries were cultivated in high-glucose Dulbecco's Modified Eagle Medium (DMEM; Thermo) supplemented with 10% (v/v) heat inactivated fetal bovine serum (FBS; Thermo), 100 U/ml penicillin/streptomycin (Pen Strep; Thermo), 10 mM HEPES buffer (Thermo) and 50 μM 2-Mercaptoethanol (Thermo). All hybridoma cultures were maintained in cell culture incubators at a constant temperature of 37° C. in humidified air with 5% $CO_2$. Hybridoma cells were typically cultured in 10 ml of medium in T-25 flasks (TPP, 90026) and passaged every 48/72 h. All hybridoma cell lines were confirmed annually to be *Mycoplasma*-free (Universal *Mycoplasma* Detection Kit, ATCC, 30-1012K). The cell line PnP-mRuby/Cas9 was published in Mason et al., 2018.

J. Generation of Antibody Libraries by Crispr-Cas9 Homology-Directed Repair

Candidate $V_H$ genes were ordered from Twist Bioscience as gene fragments, which were resuspended in 25 ul Tris-EDTA, pH 7.4 (Sigma) prior to use. All oligonucleotides as well as crRNA-JP and tracrRNA used in this study were purchased from Integrated DNA Technologies (IDT) and adjusted to 100 μM (oligonucleotides) with Tris-EDTA or to 200 μM (crRNA/tracrRNAs) with nuclease-free duplex buffer (IDT, 11-01-03-01) prior to use. The homology-directed repair (HDR) donor template used throughout this study was based on a pUC57(Kan)-HEL23-HDR homology donor plasmid. Two consecutive stop codons were incorporated into the beginning of the coding regions for the $V_H$ and the variable light chain ($V_L$) sequences in order to avoid library cloning artefacts and background antibody expression due to unmodified parental vector DNA.

For each candidate $V_H$, separate HDR-donor $V_L$ libraries were assembled in a stepwise manner by Gibson cloning using the Gibson Assembly Master Mix (NEB). When necessary, fragments were amplified using the KAPA Hifi HotStart Ready Mix (KAPA Biosystems) following manufacturer instructions. First, heavy-chain genes were amplified from gene fragments and cloned into the PCR-linearized parental HDR-donor vector (step 1). Next, with total bone-marrow RNA of a mouse that was immunized with one of the four respective antigens RT was performed using the Maxima Reverse Transcriptase (Thermo) with a degenerate primer specific for $V_L$ constant region. The resulting cDNA was used to amplify the respective $V_L$ repertoires in multiplex PCR reactions using a degenerate multiplex primer (Table 7). Finally, $V_L$ repertoires were cloned into the PCR-linearized HDR-donor vector created in step 1 for each candidate $V_H$ library (step 2) and final libraries were assessed in terms of diversity and background clones. Typically, fixed $V_H$ HDR-donor $V_L$ library sizes ranged from 30,000-80,000 transformants per library.

TABLE 7

| Primers used for Library Generation and Sequencing | | |
|---|---|---|
| Oligonucleotide ID | Step | Oligonucleotide sequence |
| crRNA-JP | cut mRuby | mG*mU*mC*rArUrGrGrArArGrGrUrUrCrGrGrUrCrA rArGrUrUrUrArGrArGrCrUrArU*mG*mC*mU |
| DN_VHscreenSF_GA_ PnPs1_fw | Amplification from Twist gene fragment | CCTTCCGGGGATCCTG |
| DN_VHscreenSF_GA_ PnPs1_rev | | CCTGGAGAGGCCATTCTTAC |
| CP399 | HDR donor linearization for HC cloning (step 1) | AAGAATGGCCTCTCCAGGTCTTTATTTTTAAC |
| CP400 | | TGACAGGATCCCCGGAAGG |
| SF_062 | LC RT primer | CACACSASTGWGGC |
| DN_LC_lib_GA_fw | HDR donor | GGCCCCAACTGTATCCAT |
| DN_LC_lib_GA_rev | linearization for LC cloning (step 2) | CCGGGACATTATAACTGAAGC |
| DN_MLC_V_GA_fw1 | LC multiplex fw | GCTTCAGTTATAATGTCCCGGGGGGAYATCCAGCTGACTCA GCC |
| DN_MLC_V_GA_fw2 | | GCTTCAGTTATAATGTCCCGGGGGGAYATTGTTCTCWCCCA GTC |
| DN_MLC_V_GA_fw3 | | GCTTCAGTTATAATGTCCCGGGGGGAYATTGTGMTMACTC AGTC |
| DN_MLC_V_GA_fw4 | | GCTTCAGTTATAATGTCCCGGGGGGAYATTGTGYTRACACA GTC |
| DN_MLC_V_GA_fw5 | | GCTTCAGTTATAATGTCCCGGGGGGAYATTGTRATGACMC AGTC |
| DN_MLC_V_GA_fw6 | | GCTTCAGTTATAATGTCCCGGGGGGAYATTMAGATRAMCC AGTC |
| DN_MLC_V_GA_fw7 | | GCTTCAGTTATAATGTCCCGGGGGGAYATTCAGATGAYDC AGTC |
| DN_MLC_V_GA_fw8 | | GCTTCAGTTATAATGTCCCGGGGGGAYATYCAGATGACAC AGAC |
| DN_MLC_V_GA_fw9 | | GCTTCAGTTATAATGTCCCGGGGGGAYATTGTTCTCAWCC AGTC |
| DN_MLC_V_GA_fw10 | | GCTTCAGTTATAATGTCCCGGGGGGAYATTGWGCTSACCC AATC |
| DN_MLC_V_GA_fw11 | | GCTTCAGTTATAATGTCCCGGGGGGAYATTSTRATGACCCA RTC |
| DN_MLC_V_GA_fw12 | | GCTTCAGTTATAATGTCCCGGGGGGAYRTTKTGATGACCCA RAC |
| DN_MLC_V_GA_fw13 | | GCTTCAGTTATAATGTCCCGGGGGGAYATTGTGATGCBCAG KC |
| DN_MLC_V_GA_fw14 | | GCTTCAGTTATAATGTCCCGGGGGGAYATTGTGATAACYCA GGA |
| DN_MLC_V_GA_fw15 | | GCTTCAGTTATAATGTCCCGGGGGGAYATTGTGATGACCCA GWT |
| DN_MLC_V_GA_fw16 | | GCTTCAGTTATAATGTCCCGGGGGGAYATTGTGATGACACA ACC |
| DN_MLC_V_GA_fw17 | | GCTTCAGTTATAATGTCCCGGGGGGAYATTTTGCTGACTCA GTC |
| DN_MLC_V_GA_fw18 | | GCTTCAGTTATAATGTCCCGGGGGGARGCTGTTGTGACTCA GGAATC |
| DN_MLC_J_GA_rev1 | LC multiplex rev | ATGGATACAGTTGGGGCCGCGTCGGCCCGTTTGATTTCCAG CTTGG |
| DN_MLC_J_GA_rev2 | | ATGGATACAGTTGGGGCCGCGTCGGCCCGTTTTATTTCCAG CTTGG |
| DN_MLC_J_GA_rev3 | | ATGGATACAGTTGGGGCCGCGTCGGCCCGTTTTATTTCCAA CTTTG |
| DN_MLC_J_GA_rev4 | | ATGGATACAGTTGGGGCCGCGTCGGCCCGTTTCAGCTCCAG CTTGG |
| DN_MLC_J_GA_rev5 | | ATGGATACAGTTGGGGCCGCGTCGGCCCGTAGGACAGTCA GTTTGG |
| DN_MLC_J_GA_rev6 | | ATGGATACAGTTGGGGCCGCGTCGGCCCGTAGGACAGTGA CCTTGG |
| CP467 | Hybridoma genotyping | CATGTGCCTTTTCAGTGCTTTCTC |
| CP468 | | CTAGATGCCTTTCTCCCTTGACTC |
| CP99 | LC Sanger sequencing | GAAAACAACATATGACTCCTGTCTTC |

TABLE 7-continued

| Primers used for Library Generation and Sequencing | | |
|---|---|---|
| Oligonucleotide ID | Step | Oligonucleotide sequence |
| CP168 | HC Sanger sequencing | TGACCTTCTCAAGTTGGC |

PnP-mRuby/Cas9 cells were electroporated with the 4D-Nucleofector System (Lonza) using the SF Cell Line 4D-Nucleofector Kit L (Lonza, V4XC-2012) with the program CQ-104. For each HDR-donor library, $10^6$ cells were harvested by centrifugation at 125 g for 10 min, washed with 1 ml of Opti-MEM Reduced Serum Medium (Thermo, 31985-062) and centrifuged again using the same parameters. The cells were finally resuspended in 100 μl of nucleofection mix containing 500 pmol of crRNA-J/tracrRNA complex and 20 μg of HDR-donor plasmid (5.9 kb) diluted in SF buffer. Following electroporation, cells were cultured in 1 ml of growth media in 24-well plates (Thermo) for two days and moved to 6-well plates (Costar) containing another 2 ml of growth media for one additional day.

K. Screening of Hybridoma Antibody Libraries by Flow Cytometry

Flow-cytometry-based analysis and cell isolation of CRISPR-Cas9 modified hybridomas was performed on a BD LSR Fortessa and BD FACS Aria III (BD Biosciences). Flow cytometry data were analyzed using FlowJo V10 (FlowJo LLC). Three days post-transfection, hybridoma cell libraries specific for one antigen were pooled and enriched for antibody-expressing and antigen-specific cells in consecutive rounds of fluorescence activated cell sorting (FACS). Typically, the number of sorted cells from the previous enrichment-step was over-sampled by a factor of 40 in terms of the number of labelled cells for the subsequent sorting-step. For labelling, cells were washed with PBS (Thermo, 10010023), incubated with the labelling antibodies or antigen for 30 min on ice protected from light, washed two times with PBS again and analyzed or sorted. The labelling reagents and working concentrations are listed in the Table 8. For cell numbers different from 106, the amount of antibody/antigen as well as the incubation volume were adjusted proportionally. For labelling of RSVF-specific cells, a two-step labelling procedure was necessary due to the indirect labeling of cells with RSVF-biotin/Streptavidin-AlexaFluor647.

TABLE 8

| Labelling Agents for FACS | | | | | |
|---|---|---|---|---|---|
| Target/Antigen | Working concentration | Dilution from stock | Incubation volume | Fluorophore | Product ID |
| anti-IgG2c | 13 μg/ml | 1:100 | 100 μl | AlexaFluor 488 | 115-545-208 (Jackson ImmunoResearch) |
| anti-IgK | 2.5 μg/ml | 1:80 | 100 μl | Brilliant Violet 421 | 409511 (BioLegend) |
| Hen egg lysozyme | 0.99 μg/ml | 1:50 | 100 μl | AlexaFluor 647 | 62971-10G-F (Sigma) |
| Ovalbumine | 1.5 μg/ml | 1:50 | 100 μl | AlexaFluor 647 | A5503 (Sigma) |
| Blue carrier protein | 1.2 μg/ml | 1:50 | 100 μl | AlexaFluor 647 | 77130 (Thermo) |
| RSV-F-DS2-biotin | 14 μg/ml | 1:50 | 100 μl | — | — |
| Streptavidin | 5 μg/ml | 1:100 | 100 μl | AlexaFluor 647 | 405237 (BioLegend) |

L. Genotyping of Single-Cell Hybridoma Clones

Genomic DNA of single cell hybridoma clones was isolated from $5\times10^5$ cells, which were washed with PBS and resuspended in QuickExtract DNA Extraction Solution (Epicentre, QE09050). Cells were incubated at 68° C. for 15 min and 95° C. for 8 min and the integrated synthetic VL-Ck-2A-VH antibody region was PCR-amplified with flanking primers CATGTGCCTTTTCAGTGCTTTCTC (SEQ ID NO: 33) and CTAGATGCCTTTCTCCCTTGACTC (SEQ ID NO: 34) that were specific for 5' and 3' homology arms. From this single amplicon, both VH and VL regions could be Sanger-sequenced using primers TGACCTTCTCAAGTTGGC (SEQ ID NO: 36) and GAAAACAACATATGACTCCTGTCTTC (SEQ ID NO: 35), respectively (Microsynth).

M. Measurement of Antibody Specificity by ELISA

Standard sandwich enzyme-linked immunosorbent assays (ELISAs) were performed to measure the specificity of single hybridoma cell line supernatants containing secreted IgG. High binding 96-well plates (Costar, CLS3590) were coated over night with 4 μg/ml of antigen in PBS at 4° C. The plates were then blocked for two hours at room temperature with PBS containing 2% (m/v) non-fat dried milk powder (AppliChem, A0830) and 0.05% (v/v) Tween-20 (AppliChem, A1389). After blocking, plates were washed three times with PBS containing 0.05% (v/v) Tween-20 (PBST). Cell culture supernatants were 0.2 μm sterile-filtrated (Sartorius, 16534) and serially diluted across the plate (1:3 steps) in PBS supplemented with 2% (m/v) milk (PBSM), starting with non-diluted supernatants as the highest concentrations. Plates were incubated for one hour at room temperature and washed three times with PBST. HRP-conjugated rat monoclonal [187.1] anti-mouse kappa light chain antibody (abcam ab99617) was used as secondary detection antibody, concentrated at 0.7 μg/ml (1:1500 dilution from stock) in PBSM. Plates were incubated at room temperature for one hour again, followed by three washing steps with PBST. ELISA detection was performed using the 1-Step Ultra TMB-ELISA Substrate Solution (Thermo, 34028) and reaction was terminated with 1 M H2SO4. Absorption at 450 nm was measured with the Infinite 200 PRO NanoQuant (Tecan) and data were analyzed using Prism V8 (Graphpad).

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including," "comprising," "having," "containing," "involving," "characterized by," "characterized in that," and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. References to at least one of a conjunctive list of terms may be construed as an inclusive OR to indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed:

1. A method, comprising:

providing to a candidate identification system a plurality of input amino acid sequences from a library of immunoglobulin heavy chain variable region ($V_H$) sequences or a library of immunoglobulin light chain variable ($V_L$) region sequences, wherein the library comprises an entire immunoglobulin repertoire from animals immunized with an antigen;

transforming, by an encoder executed by the candidate identification system, the plurality of input amino acid sequences into a latent space, wherein the encoder uses a linear classifier, a plurality of rectified linear units, and a variational autoencoder (VAE) to transform the plurality of input amino acid sequences into the latent space, and wherein the linear classifier is a linear support vector machine (SVM) classifier of the immunized antigen exposure;

determining, by a clustering engine executed by the candidate identification system, a plurality of sequence clusters within the latent space;

identifying, by the clustering engine, a convergent sequence cluster that is predictive for the immunized antigen exposure;

selecting, by a candidate generation engine executed by the candidate identification system, within the latent space an immunized antigen-associated convergent sequence cluster;

generating, by the candidate generation engine using a decoder, a candidate amino acid sequence based on the immunized antigen-associated convergent sequence cluster, wherein the decoder comprises a plurality of different neural networks comprising a plurality of long short-term recurrent neural networks, and wherein generating the candidate amino acid sequence further comprises providing the immunized antigen-associated convergent sequence cluster to each of the plurality of long short-term recurrent neural networks; and generating a library of hybridoma cell clones expressing antibodies comprising the candidate amino acid sequence.

2. The method of claim 1, wherein the input amino acid sequences comprise amino acid sequences of a complementarity determining region (CDR) of an immunoglobulin selected from the group consisting of a heavy chain variable region ($V_H$) CDR1 (CDRH1), a heavy chain variable region ($V_H$) CDR2 (CDRH2), a heavy chain variable region ($V_H$) CDR3 (CDRH3), a light chain variable ($V_L$) region CDR1 (CDRL1), a light chain variable ($V_L$) region CDR2 (CDRL2), or a light chain variable ($V_L$) region CDR3 (CDRL3), or any combination thereof.

3. The method of claim 2, wherein the input amino acid sequences comprise CDRH3 sequences.

4. The method of claim 2, wherein the input amino acid sequences comprise CDRH1 sequences.

5. The method of claim 2, wherein the input amino acid sequences comprises CDRH2 sequences.

6. The method of claim 2, wherein the input amino acid sequences comprises CDRL1 sequences.

7. The method of claim 2, wherein the input amino acid sequences comprises CDRL2 sequences.

8. The method of claim 2, wherein the input amino acid sequences comprises CDRL3 sequences.

9. The method of claim 2, wherein the input amino acid sequences comprise amino acid sequences of a full-length immunoglobulin heavy variable region, or antigen binding portions thereof.

10. The method of claim 2, wherein the input amino acid sequences comprise amino acid sequences of a full-length immunoglobulin light variable region, or antigen binding portions thereof.

11. The method of claim 1, comprising: transforming the plurality of input amino acid sequences into the latent space with variational deep embedding (VaDE).

12. The method of claim 1, comprising: determining the plurality of sequence clusters with mixture modeling.

13. The method of claim 12, wherein the mixture modeling comprises Gaussian Mixture Modeling (GMM).

14. The method of claim 1, wherein the animals were immunized with at least 1, at least 2, at least 3, or at least 4 different antigens.

15. The method of claim 1, wherein the library comprises entire immunoglobulin repertoires from at least 10, at least 20, at least 30, at least 40, or at least 50 immunized animals.

16. The method of claim 1, wherein:

(a) transforming comprises padding each of the plurality of input amino acid sequences, one-hot encoding padded input amino acid sequences, and concatenating the one-hot encoded input amino acid sequences; and (b) the encoder uses a linear classifier, a plurality of rectified linear units, and a variational autoencoder (VAE) to transform the concatenated, one-hot encoded, and padded sequences into a latent space.

17. The method of claim 16, wherein the decoder generates the candidate amino acid sequence by mapping the input amino acid sequence and the concatenated one-hot encoded amino acid sequence with a rectified linear unit (ReLU) activation.

18. The method of claim 1, wherein the candidate amino acid sequence is a convergent amino acid sequence from the immunized antigen-associated convergent sequence cluster.

19. The method of claim 1, wherein the candidate amino acid sequence is an in sillico generated amino acid sequence based on the immunized antigen-associated convergent sequence cluster.

* * * * *

SEQUENCE LISTING

```
<160> NUMBER OF SEQ ID NOS: 143

<210> SEQ ID NO 1
<211> LENGTH: 36
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 1
```

gucauggaag guucggucaa guuuuagagc uaugcu 36

<210> SEQ ID NO 2
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 2
ccttccgggg atcctg 16

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 3
cctggagagg ccattcttac 20

<210> SEQ ID NO 4
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 4
aagaatggcc tctccaggtc tttattttta ac 32

<210> SEQ ID NO 5
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 5
tgacaggatc cccggaagg 19

<210> SEQ ID NO 6
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 6
cacacsastg wggc 14

<210> SEQ ID NO 7
<211> LENGTH: 18
<212> TYPE: DNA
<213> ORGANISM: Artificial Sequence
<220> FEATURE:

<221> NAME/KEY: source
<223> OTHER INFORMATION: /note="Description of Artificial Sequence: Synthetic primer"

<400> SEQUENCE: 7
ggccccaact gtatccat 18

<210> SEQ ID NO 8
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 8
ccgggacatt ataactgaag c 21

<210> SEQ ID NO 9
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 9
gcttcagtta taatgtcccg gggggayatc cagctgactc agcc 44

<210> SEQ ID NO 10
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 10
gcttcagtta taatgtcccg gggggayatt gttctcwccc agtc 44

<210> SEQ ID NO 11
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 11
gcttcagtta taatgtcccg gggggayatt gtgmtmactc agtc 44

<210> SEQ ID NO 12
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
gcttcagtta taatgtcccg gggggayatt gtgytracac agtc 44

```
<210> SEQ ID NO 13
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 13

gcttcagtta taatgtcccg gggggayatt gtratgacmc agtc                    44


<210> SEQ ID NO 14
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 14

gcttcagtta taatgtcccg gggggayatt magatramcc agtc                    44


<210> SEQ ID NO 15
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15

gcttcagtta taatgtcccg gggggayatt cagatgaydc agtc                    44


<210> SEQ ID NO 16
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16

gcttcagtta taatgtcccg gggggayaty cagatgacac agac                    44


<210> SEQ ID NO 17
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17

gcttcagtta taatgtcccg gggggayatt gttctcawcc agtc                    44


<210> SEQ ID NO 18
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

<400> SEQUENCE: 18
gcttcagtta taatgtcccg gggggayatt gwgctsaccc aatc 44

<210> SEQ ID NO 19
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 19
gcttcagtta taatgtcccg gggggayatt stratgaccc artc 44

<210> SEQ ID NO 20
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 20
gcttcagtta taatgtcccg gggggayrtt ktgatgaccc arac 44

<210> SEQ ID NO 21
<211> LENGTH: 43
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 21
gcttcagtta taatgtcccg gggggayatt gtgatgcbca gkc 43

<210> SEQ ID NO 22
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 22
gcttcagtta taatgtcccg gggggayatt gtgataacyc agga 44

<210> SEQ ID NO 23
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 23
gcttcagtta taatgtcccg gggggayatt gtgatgaccc agwt 44

<210> SEQ ID NO 24
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 24
gcttcagtta taatgtcccg gggggayatt gtgatgacac aacc 44

<210> SEQ ID NO 25
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 25
gcttcagtta taatgtcccg gggggayatt ttgctgactc agtc 44

<210> SEQ ID NO 26
<211> LENGTH: 47
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 26
gcttcagtta taatgtcccg gggggargct gttgtgactc aggaatc 47

<210> SEQ ID NO 27
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 27
atggatacag ttggggccgc gtcggcccgt ttgatttcca gcttgg 46

<210> SEQ ID NO 28
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 28
atggatacag ttggggccgc gtcggcccgt tttatttcca gcttgg 46

<210> SEQ ID NO 29
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic primer"

<400> SEQUENCE: 29
atggatacag ttggggccgc gtcggcccgt tttatttcca actttg 46

<210> SEQ ID NO 30
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 30
atggatacag ttggggccgc gtcggcccgt ttcagctcca gcttgg 46

<210> SEQ ID NO 31
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 31
atggatacag ttggggccgc gtcggcccgt aggacagtca gtttgg 46

<210> SEQ ID NO 32
<211> LENGTH: 46
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 32
atggatacag ttggggccgc gtcggcccgt aggacagtga ccttgg 46

<210> SEQ ID NO 33
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 33
catgtgcctt ttcagtgctt tctc 24

<210> SEQ ID NO 34
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 34
ctagatgcct ttctcccttg actc 24

<210> SEQ ID NO 35
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 35
gaaaacaaca tatgactcct gtcttc 26

<210> SEQ ID NO 36
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 36
tgaccttctc aagttggc 18

<210> SEQ ID NO 37
<211> LENGTH: 52
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 37
atcggactta agcttggcgc actagccgca ttttcagggc aaagcatcat ta 52

<210> SEQ ID NO 38
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 38

Asn Ala Trp Asp Gly Asn Leu Asp Tyr
1 5

<210> SEQ ID NO 39
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

Ala Arg Arg Ser Tyr Gly Ser Ser Leu Asp Tyr
1 5 10

<210> SEQ ID NO 40
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 40

Ala Arg Gly Gly Asn Pro Ala Trp Phe Ala Tyr
1 5 10

<210> SEQ ID NO 41
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 41

Gly Tyr Thr Phe Thr Asp Tyr Glu
1 5

<210> SEQ ID NO 42
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 42

Ile Asn Pro Glu Thr Gly Gly Thr
1 5

<210> SEQ ID NO 43
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 43

Thr Arg Ser Thr Gly His Phe Asp Tyr
1 5

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 44

Gly Tyr Pro Phe Thr His Tyr Gly
1 5

<210> SEQ ID NO 45
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 45

Thr Asn Ile Tyr Thr Gly Glu Pro Thr
1 5

<210> SEQ ID NO 46
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 46

Ala Arg Val Gly Gly Ser Ser Gln Pro Leu Ala Tyr
1 5 10

<210> SEQ ID NO 47
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 47

Gly Tyr Thr Phe Thr Ser Tyr Tyr
1 5

<210> SEQ ID NO 48
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 48

Ile Asn Pro Ser Asn Gly Gly Thr
1 5

<210> SEQ ID NO 49
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 49

Ala Arg Gly Tyr Gly Tyr Phe Asp Tyr
1 5

<210> SEQ ID NO 50
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 50

Gly Tyr Thr Phe Thr Asn Tyr Gly
1 5

<210> SEQ ID NO 51
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 51

```
Ile Asn Thr Tyr Thr Gly Glu Pro Thr
1               5
```

<210> SEQ ID NO 52
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 52

```
Ala Arg Ser Glu Gly Asn Tyr Tyr Gly Leu Ala Tyr
1               5                   10
```

<210> SEQ ID NO 53
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 53

```
Ala Arg Gly Asn Tyr Gly Asn Ser Leu Asp Tyr
1               5                   10
```

<210> SEQ ID NO 54
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 54

```
Ala Arg Gly Gly Tyr Gly Ser Ser Phe Asp Cys
1               5                   10
```

<210> SEQ ID NO 55
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 55

```
Ala Arg Gly Gly Tyr Val Ser Ser Leu Asp Tyr
1               5                   10
```

<210> SEQ ID NO 56
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 56

```
Thr Arg Gly Gly Tyr Gly Ser Ser Leu Asp Tyr
```

1 5 10

<210> SEQ ID NO 57
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 57

Ala Arg Gly His Tyr Gly Ser Ser Leu Asp Cys
1 5 10

<210> SEQ ID NO 58
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 58

Ala Arg Gly Phe Tyr Val Asn Ser Leu Asp Tyr
1 5 10

<210> SEQ ID NO 59
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Ala Arg Gly Lys Tyr Gly Asn Ser Leu Asp Tyr
1 5 10

<210> SEQ ID NO 60
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Ala Arg Gly Ala Tyr Gly Asn Ser Phe Asp Tyr
1 5 10

<210> SEQ ID NO 61
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 61

Ala Arg Gly His Tyr Ser Ser Ser Leu Asp Tyr
1 5 10

<210> SEQ ID NO 62

<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 62

Ala Arg Gly His Tyr Gly Asn Ser Leu Asp Phe
1 5 10

<210> SEQ ID NO 63
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Ala Arg Gly Gly Tyr Gly Asn Ser Phe Asp Tyr
1 5 10

<210> SEQ ID NO 64
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 64

Ala Arg Gly Gly Tyr Gly Ser Asn Leu Asp Tyr
1 5 10

<210> SEQ ID NO 65
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 65

Ala Arg Gly Tyr Tyr Gly Ser Ser Phe Asp Tyr
1 5 10

<210> SEQ ID NO 66
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 66

Ala Arg Gly Tyr Tyr Gly Asn Ser Leu Asp Tyr
1 5 10

<210> SEQ ID NO 67
<211> LENGTH: 11
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic peptide"

<400> SEQUENCE: 67

Ala Arg Gly His Tyr Gly Asn Ser Phe Asp Tyr
1               5                   10


<210> SEQ ID NO 68
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 68

Ala Arg Gly Lys Tyr Gly Ser Ser Leu Asp Tyr
1               5                   10


<210> SEQ ID NO 69
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ala Arg Gly Tyr Tyr Val Ser Ser Leu Asp Tyr
1               5                   10


<210> SEQ ID NO 70
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Ala Arg Gly Gly Tyr Gly Asn Ser Leu Asp Phe
1               5                   10


<210> SEQ ID NO 71
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Ala Arg Gly Ile Tyr Gly Asn Ser Leu Asp Tyr
1               5                   10


<210> SEQ ID NO 72
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 72

Ala Arg Ser Gly Tyr Gly Ser Ser Leu Asp Tyr
1 5 10

<210> SEQ ID NO 73
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 73

Ala Arg Ser His Tyr Gly Ser Ser Leu Asp Tyr
1 5 10

<210> SEQ ID NO 74
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 74

Ala Arg Gly Gly Tyr Gly Asn Ser Leu Gly Tyr
1 5 10

<210> SEQ ID NO 75
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 75

Ala Arg Gly Phe Tyr Gly Asn Ser Leu Ala Tyr
1 5 10

<210> SEQ ID NO 76
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 76

Gly Tyr Ala Phe Ser Ser Tyr Trp
1 5

<210> SEQ ID NO 77
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 77

Ile Asn Pro Gly Asp Gly Asp Thr
1 5

<210> SEQ ID NO 78
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 78

```
Cys Ala Arg Gly Gly Tyr Gly Ser Phe Ala Tyr Trp
1               5                   10
```

<210> SEQ ID NO 79
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 79

```
Gly Tyr Ile Phe Thr Ser Tyr Trp
1               5
```

<210> SEQ ID NO 80
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 80

```
Ile Tyr Pro Gly Thr Gly Ser Ser
1               5
```

<210> SEQ ID NO 81
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 81

```
Cys Ala Arg Ala Glu Tyr Asp Ser Ser Tyr Ala Met Asp Phe Trp
1               5                   10                  15
```

<210> SEQ ID NO 82
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 82

```
Ile Tyr Pro Gly Thr Gly Ser Thr
1               5
```

<210> SEQ ID NO 83
<211> LENGTH: 14

<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 83

Cys Ala Arg Gly Asp Tyr Gly Ser Ser Tyr Phe Asp Tyr Trp
1 5 10

<210> SEQ ID NO 84
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 84

Cys Ala Arg Asn Gly Asp Tyr Ala Met Asp Tyr Trp
1 5 10

<210> SEQ ID NO 85
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 85

Cys Thr Arg Gly Gly Tyr Gly Ser Phe Ala Tyr Trp
1 5 10

<210> SEQ ID NO 86
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 86

Cys Ala Ile Thr Thr Val Asn Ala Met Asp Tyr Trp
1 5 10

<210> SEQ ID NO 87
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 87

Gly Phe Asn Ile Lys Asp Tyr Tyr
1 5

<210> SEQ ID NO 88
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 88

Ile Asp Pro Glu Asn Gly Asp Thr
1 5

<210> SEQ ID NO 89
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 89

Cys Asn Ala Trp Asp Gly Asn Leu Asp Tyr Trp
1 5 10

<210> SEQ ID NO 90
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 90

Gly Phe Ser Leu Ser Thr Ser Gly Met Gly
1 5 10

<210> SEQ ID NO 91
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 91

Ile Tyr Trp Asp Asp Asp Lys
1 5

<210> SEQ ID NO 92
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 92

Cys Ala Arg Arg Ser Tyr Gly Ser Ser Leu Asp Tyr Trp
1 5 10

<210> SEQ ID NO 93
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"

<400> SEQUENCE: 93

```
Gly Phe Ser Leu Thr Asp Tyr Gly
1               5


<210> SEQ ID NO 94
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Ile Trp Gly Asp Gly Ser Thr
1               5


<210> SEQ ID NO 95
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 95

Cys Ala Arg Gly Asn Tyr Gly Asn Ser Leu Asp Tyr Trp
1               5                   10


<210> SEQ ID NO 96
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Asn Pro Gly Asp Gly Asp Thr Tyr Asn Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Asn Asn Leu Thr Ser Lys Asp Ser Ala Val Tyr Phe Cys
                85                  90                  95

Ala Arg Gly Gly Tyr Gly Ser Phe Ala Tyr Trp Gly Gln Gly Thr Leu
            100                 105                 110

Val Thr Val Ser Ala
        115


<210> SEQ ID NO 97
<211> LENGTH: 120
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 97

```
Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Thr Gly Ser Ser Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Arg Ala Glu Tyr Asp Ser Ser Tyr Ala Met Asp Phe Trp Gly Gln
            100                 105                 110

Gly Thr Ser Val Thr Val Ser Ser
        115                 120
```

<210> SEQ ID NO 98
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 98

```
Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Thr Gly Ser Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Arg Gly Asp Tyr Gly Ser Ser Tyr Phe Asp Tyr Trp Gly Gln Gly
            100                 105                 110

Thr Thr Leu Thr Val Ser Ser
        115
```

<210> SEQ ID NO 99
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 99

```
Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
```

```
            20                  25                  30

Trp Ile His Trp Val Lys Gln Arg Ser Gly Gln Gly Leu Glu Trp Ile
        35                  40                  45

Ala Arg Ile Tyr Pro Gly Thr Gly Ser Thr Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Arg Asn Gly Asp Tyr Ala Met Asp Tyr Trp Gly Gln Gly Thr Ser
            100                 105                 110

Val Thr Val Ser Ser
        115


<210> SEQ ID NO 100
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 100

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Met Tyr Trp Val Lys Gln Arg Pro Gly Gln Gly Leu Glu Trp Ile
        35                  40                  45

Gly Glu Ile Asn Pro Ser Asn Gly Gly Thr Asn Phe Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Gly Gly Tyr Gly Ser Phe Ala Tyr Trp Gly Gln Gly Thr Leu
            100                 105                 110

Val Thr Val Ser Ala
        115


<210> SEQ ID NO 101
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 101

Gln Val Gln Leu Gln Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Thr Gly Ser Thr Tyr Tyr Asn Glu Lys Phe
    50                  55                  60
```

```
Lys Gly Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Ile Thr Thr Val Asn Ala Met Asp Tyr Trp Gly Gln Gly Thr Ser
            100                 105                 110

Val Thr Val Ser Ser
        115


<210> SEQ ID NO 102
<211> LENGTH: 116
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 102

Glu Val Gln Leu Gln Gln Ser Gly Ala Glu Leu Val Arg Ser Gly Ala
1               5                   10                  15

Ser Val Lys Leu Ser Cys Thr Ala Ser Gly Phe Asn Ile Lys Asp Tyr
            20                  25                  30

Tyr Ile His Trp Val Lys Gln Arg Pro Glu Gln Gly Leu Glu Trp Ile
        35                  40                  45

Gly Trp Ile Asp Pro Glu Asn Gly Asp Thr Glu Tyr Ala Pro Lys Phe
    50                  55                  60

Gln Asp Lys Ala Thr Met Thr Ala Asp Thr Ser Ser Asn Thr Ala Tyr
65                  70                  75                  80

Leu Gln Leu Ser Ser Leu Thr Ser Gly Asp Thr Ala Val Tyr Tyr Cys
                85                  90                  95

Asn Ala Trp Asp Gly Asn Leu Asp Tyr Trp Gly Gln Gly Thr Ser Val
            100                 105                 110

Thr Val Ser Ser
        115


<210> SEQ ID NO 103
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 103

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Phe Leu Lys Ile Thr Ser Val Asp Thr Ala Asp Thr Ala Thr Tyr Tyr
                85                  90                  95
```

```
Cys Ala Arg Arg Ser Tyr Gly Ser Ser Leu Asp Tyr Trp Gly Gln Gly
            100                 105                 110

Thr Thr Leu Thr Val Ser Ser
        115


<210> SEQ ID NO 104
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 104

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Ile Ser Lys Ser Gln Val Phe Leu
65                  70                  75                  80

Lys Met Asn Ser Leu Gln Thr Asp Asp Thr Ala Lys Tyr Tyr Cys Ala
                85                  90                  95

Arg Gly Asn Tyr Gly Asn Ser Leu Asp Tyr Trp Gly Gln Gly Thr Thr
            100                 105                 110

Leu Thr Val Ser Ser
        115


<210> SEQ ID NO 105
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 105

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Tyr Gly Ser Ser Phe Asp Cys Trp Gly Gln Gly Thr Thr
            100                 105                 110

Leu Thr Val Ser Ser
        115
```

```
<210> SEQ ID NO 106
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 106

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Tyr Val Ser Ser Leu Asp Tyr Trp Gly Gln Gly Thr Thr
            100                 105                 110

Leu Thr Val Ser Ser
        115


<210> SEQ ID NO 107
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 107

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Tyr
            20                  25                  30

Gly Ile Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Thr Tyr Tyr Cys Thr
                85                  90                  95

Arg Gly Gly Tyr Gly Ser Ser Leu Asp Tyr Trp Gly Gln Gly Thr Thr
            100                 105                 110

Leu Thr Val Ser Ser
        115


<210> SEQ ID NO 108
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
```

Synthetic polypeptide"

<400> SEQUENCE: 108

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Ser Pro Gly Lys Gly Leu Glu Trp Leu
        35                  40                  45

Gly Met Ile Trp Gly Asp Gly Ser Thr Asp Tyr Ser Ser Ala Leu Lys
    50                  55                  60

Ser Arg Leu Thr Ile Ser Lys Asp Asn Ser Lys Ser Gln Val Phe Leu
65                  70                  75                  80

Lys Met Asn Ser Leu Gln Ile Asp Asp Thr Ala Arg Tyr Tyr Cys Ala
                85                  90                  95

Arg Gly His Tyr Gly Ser Ser Leu Asp Cys Trp Gly Gln Gly Thr Thr
            100                 105                 110

Leu Thr Val Ser Ser
        115
```

<210> SEQ ID NO 109
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 109

```
Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Asp Phe
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser His Val Phe Leu
65                  70                  75                  80

Lys Met Asn Ser Leu Gln Thr Asp Asp Thr Ala Arg Tyr Tyr Cys Ala
                85                  90                  95

Arg Gly Phe Tyr Val Asn Ser Leu Asp Tyr Trp Gly Gln Gly Thr Leu
            100                 105                 110

Val Thr Val Ser Ala
        115
```

<210> SEQ ID NO 110
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 110

```
Gln Val Gln Leu Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Ser Ser Ala Leu Arg
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Lys Tyr Gly Asn Ser Leu Asp Tyr Trp Gly Gln Gly Thr Thr
            100                 105                 110

Leu Thr Val Ser Ser
        115


<210> SEQ ID NO 111
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 111

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Thr Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly His Tyr Ser Ser Ser Leu Asp Tyr Trp Gly Gln Gly Thr Thr
            100                 105                 110

Leu Thr Val Ser Ser
        115


<210> SEQ ID NO 112
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 112

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
```

```
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Arg Gly Tyr Tyr Gly Ser Ser Leu Asp Tyr Trp Gly Gln Gly Thr Thr
            100                 105                 110

Leu Thr Val Ser Ser
        115


<210> SEQ ID NO 113
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 113

Gln Val Gln Leu Lys Glu Ser Gly Pro Gly Leu Val Thr Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Arg Gly Leu Glu Trp Leu
        35                  40                  45

Gly Met Ile Trp Gly Asp Gly Thr Thr Asp Tyr Asn Ser Pro Leu Lys
    50                  55                  60

Ser Arg Leu Asn Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly His Tyr Gly Asn Ser Leu Asp Phe Trp Gly Gln Gly Thr Thr
            100                 105                 110

Leu Thr Val Ser Ser
        115


<210> SEQ ID NO 114
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 114

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95
```

```
Arg Gly Gly Tyr Gly Asn Ser Phe Asp Tyr Trp Gly Gln Gly Thr Thr
            100                 105                 110

Leu Thr Val Ser Ser
        115


<210> SEQ ID NO 115
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 115

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Gly Tyr Gly Ser Asn Leu Asp Tyr Trp Gly Gln Gly Thr Thr
            100                 105                 110

Leu Thr Val Ser Ser
        115


<210> SEQ ID NO 116
<211> LENGTH: 117
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 116

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Gly Ser Thr Asp Tyr Asn Ser Ala Leu Lys
    50                  55                  60

Ser Arg Met Ser Ile Ser Lys Asp Asp Ser Lys Ser Gln Val Phe Leu
65                  70                  75                  80

Lys Met Asn Ser Leu Gln Thr Asp Asp Thr Ala Arg Tyr Tyr Cys Ala
                85                  90                  95

Arg Gly Ala Tyr Gly Asn Ser Phe Asp Tyr Trp Gly Gln Gly Thr Leu
            100                 105                 110

Val Thr Val Ser Ala
        115
```

```
<210> SEQ ID NO 117
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 117

Asp Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Phe Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Leu Thr
                85                  90                  95

Phe Gly Ala Gly Thr Lys Leu Glu Ile Lys
            100                 105


<210> SEQ ID NO 118
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 118

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Phe Met Asn Trp Tyr Gln Gln Lys Pro Gly Gln Pro Pro
        35                  40                  45

Lys Leu Leu Ile Lys Ser Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Ile Lys
            100                 105                 110


<210> SEQ ID NO 119
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 119

Asp Ile Val Met Thr Gln Ser Pro Ala Ser Leu Ala Val Ser Leu Gly
```

```
1               5                   10                  15

Gln Arg Ala Thr Ile Ser Cys Arg Ala Ser Gln Ser Val Ser Thr Ser
            20                  25                  30

Ser Tyr Ser Phe Met His Trp Tyr Gln Gln Lys Pro Gly Gln Pro Pro
        35                  40                  45

Lys Leu Leu Ile Lys Ser Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Ile Lys
            100                 105                 110


<210> SEQ ID NO 120
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 120

Asp Ile Val Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Phe Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Leu Lys
            100                 105                 110


<210> SEQ ID NO 121
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 121

Asp Ile Leu Met Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30

Phe Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80
```

```
Asp Ala Ala Thr Tyr Tyr Cys Gln Gln Tyr His Ser Tyr Pro Leu Thr
                85                  90                  95

Phe Gly Ser Gly Thr Lys Leu Glu Ile Lys
            100                 105


<210> SEQ ID NO 122
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 122

Asp Ile Gln Met Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser His Met Asn Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Ile Tyr Tyr Cys Gln His Ser Trp
                85                  90                  95

Glu Met Pro Tyr Thr Phe Gly Gly Gly Thr Lys Leu Glu Ile Lys
            100                 105                 110


<210> SEQ ID NO 123
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 123

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Pro Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Ile Lys
            100                 105


<210> SEQ ID NO 124
<211> LENGTH: 107
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic polypeptide"

<400> SEQUENCE: 124

Asp Ile Val Met Thr Gln Ser Pro Ser Ser Met Tyr Ala Ser Leu Gly
1               5                   10                  15

Glu Arg Val Thr Ile Thr Cys Lys Ala Ser Gln Asp Ile Lys Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 125
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 125

Asp Ile Gln Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 126
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 126

Asp Ile Val Leu Thr Gln Ser His Lys Phe Met Ser Thr Ser Val Gly
1               5                   10                  15

Asp Arg Val Ser Ile Thr Cys Lys Ala Ser Gln Asp Val Gly Ser Ala
            20                  25                  30

Val Ala Trp Tyr Gln Gln Lys Pro Gly Gln Ser Pro Lys Leu Leu Ile
```

```
        35                  40                  45

Tyr Trp Ala Ser Thr Arg Arg Thr Gly Val Pro Asp Arg Phe Thr Gly
    50                  55                  60

Ser Gly Ser Gly Thr Asp Phe Thr Leu Thr Ile Asn Asn Val Gln Ser
65                  70                  75                  80

Glu Asp Leu Ala Asp Tyr Phe Cys His Gln Tyr Asn Thr Tyr Ser Leu
                85                  90                  95

Thr Phe Gly Ala Gly Thr Lys Leu Glu Ile Lys
            100                 105


<210> SEQ ID NO 127
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 127

Asp Ile Val Met Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Tyr Trp Tyr Gln Gln Lys Pro Gly Ser Ser Pro Arg Leu Leu Ile Tyr
        35                  40                  45

Asp Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Trp Ser Ser Tyr Pro Pro Thr
                85                  90                  95

Phe Gly Ser Gly Thr Lys Leu Glu Ile Lys
            100                 105


<210> SEQ ID NO 128
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 128

Asp Ile Val Ile Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Val Ser Gly Val Pro Gly Arg Phe Ser Gly Ser
    50                  55                  60

Gly Ser Gly Asn Ser Tyr Ser Leu Thr Ile Ser Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Ile Lys
            100                 105
```

<210> SEQ ID NO 129
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 129

```
Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Arg Tyr Met
            20                  25                  30

Cys Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser Tyr Ser Leu Thr Ile Gly Ser Met Glu Ala Glu
65                  70                  75                  80

Asp Val Ala Thr Tyr Tyr Cys Phe Gln Gly Ser Gly Tyr Pro Leu Thr
                85                  90                  95

Phe Gly Ala Gly Thr Lys Leu Glu Leu Lys
            100                 105
```

<210> SEQ ID NO 130
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 130

```
Asp Ile Gln Met Thr Gln Thr Pro Leu Ser Leu Pro Val Ser Leu Gly
1               5                   10                  15

Asn Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110
```

<210> SEQ ID NO 131
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 131

```
Asp Ile Val Met Thr Gln Thr Thr Ser Ser Leu Ser Ala Ser Leu Gly
1               5                   10                  15

Asp Arg Val Thr Ile Ser Cys Arg Ser Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Ser Asp Tyr Ser Leu Thr Ile Thr Asn Leu Glu Gln
65                  70                  75                  80

Glu Asp Ile Ala Thr Tyr Phe Cys Gln Gln Gly Asp Thr Leu Pro Tyr
                85                  90                  95

Thr Phe Gly Gly Gly Thr Lys Leu Glu Ile Lys
            100                 105


<210> SEQ ID NO 132
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 132

Asp Ile Val Met Thr Gln Ser Pro Ala Ser Gln Ser Ala Ser Leu Gly
1               5                   10                  15

Glu Ser Val Thr Ile Thr Cys Leu Ala Ser Gln Thr Ile Gly Lys Trp
            20                  25                  30

Leu Ala Trp Tyr Gln Gln Lys Pro Gly Lys Ser Pro Gln Leu Leu Ile
        35                  40                  45

Tyr Ala Ala Thr Ile Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Gly Gly Thr Lys Leu Glu Ile Lys
            100                 105


<210> SEQ ID NO 133
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 133

Asp Ile Leu Met Thr Gln Ser Pro Leu Ser Leu Pro Val Ser Leu Gly
1               5                   10                  15

Asp Gln Val Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
            100                 105                 110


<210> SEQ ID NO 134
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 134

Asp Ile Val Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Leu Lys
            100                 105


<210> SEQ ID NO 135
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 135

Asp Ile Gln Ile Asn Gln Ser Pro Ala Ser Gln Ser Ala Ser Leu Gly
1               5                   10                  15

Glu Ser Val Thr Ile Thr Cys Leu Ala Ser Gln Thr Ile Gly Lys Trp
            20                  25                  30

Leu Ala Trp Tyr Gln Gln Lys Pro Gly Lys Ser Pro Gln Leu Leu Ile
        35                  40                  45

Tyr Ala Ala Thr Ser Leu Ala Asp Gly Val Pro Ser Arg Phe Ser Gly
    50                  55                  60

Ser Gly Ser Gly Thr Lys Phe Ser Phe Lys Ile Ser Ser Leu Gln Ala
65                  70                  75                  80

Glu Asp Phe Val Ser Tyr Tyr Cys Gln Gln Leu Tyr Ser Thr Pro Leu
                85                  90                  95

Thr Phe Gly Gly Gly Thr Lys Leu Glu Ile Lys
            100                 105


<210> SEQ ID NO 136
<211> LENGTH: 8
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 136

Gly Tyr Thr Phe Thr Asp Tyr Ser
1               5


<210> SEQ ID NO 137
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ile Asn Thr Glu Thr Gly Glu Pro
1               5


<210> SEQ ID NO 138
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ala Arg Gly Gly Tyr Gly Ser Phe Ala Tyr
1               5                   10


<210> SEQ ID NO 139
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Ala Arg Ala Glu Tyr Asp Ser Ser Tyr Ala Met Asp Phe
1               5                   10


<210> SEQ ID NO 140
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 140

Ala Arg Gly Asp Tyr Gly Ser Ser Tyr Phe Asp Tyr
1               5                   10


<210> SEQ ID NO 141
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 141

Ala Arg Asn Gly Asp Tyr Ala Met Asp Tyr
1               5                   10


<210> SEQ ID NO 142
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Thr Arg Gly Gly Tyr Gly Ser Phe Ala Tyr
1               5                   10


<210> SEQ ID NO 143
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ala Ile Thr Thr Val Asn Ala Met Asp Tyr
1               5                   10
```